(12) United States Patent
Malladi et al.

(10) Patent No.: US 9,249,095 B2
(45) Date of Patent: Feb. 2, 2016

(54) 2-METHYLTHIOPYRROLIDINES AND THEIR USE FOR MODULATING BACTERIAL QUORUM SENSING

(75) Inventors: Venkata L. Malladi, Cranberry Township, PA (US); Lisa Schneper, Lititz, PA (US); Adam J. Sobczak, Easley, SC (US); Kalai Mathee, Miami, FL (US); Stanislaw F. Wnuk, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 36 days.

(21) Appl. No.: 14/125,597

(22) PCT Filed: Jun. 18, 2012

(86) PCT No.: PCT/US2012/042899
§ 371 (c)(1),
(2), (4) Date: Jan. 16, 2014

(87) PCT Pub. No.: WO2012/174511
PCT Pub. Date: Dec. 20, 2012

(65) Prior Publication Data
US 2014/0128446 A1    May 8, 2014

Related U.S. Application Data

(60) Provisional application No. 61/497,811, filed on Jun. 16, 2011.

(51) Int. Cl.
| | | |
|---|---|---|
| C07D 207/12 | (2006.01) |
| A61K 31/4025 | (2006.01) |
| C07D 207/273 | (2006.01) |
| A61K 31/40 | (2006.01) |
| C07D 207/267 | (2006.01) |

(52) U.S. Cl.
CPC ............ *C07D 207/273* (2013.01); *A61K 31/40* (2013.01); *A61K 31/4025* (2013.01); *C07D 207/12* (2013.01); *C07D 207/267* (2013.01)

(58) Field of Classification Search
CPC .......................... C07D 207/12; A61K 31/4025
See application file for complete search history.

(56) References Cited

FOREIGN PATENT DOCUMENTS

| WO | WO-00/06177 A1 | 2/2000 |
| WO | WO-01/18248 A2 | 3/2001 |

OTHER PUBLICATIONS

Malladi et al. (Bioorg. Med. Chem. 19 (2011) 5500-5506).*
Rando (CAPLUS Accession No. 1998:545380), (1998).*
Amara et al., Covalent inhibition of bacterial quorum sensing, J. Am. Chem. Soc., 131(30):10610-9 (2009).
Andersen et al., gfp-based N-acyl homoserine-lactone sensor systems for detection of bacterial communication, Appl. Environ. Microbiol., 67(2):575-85 (2001).
Andersen et al., New unstable variants of green fluorescent protein for studies of transient gene expression in bacteria, Appl. Environ. Microbiol., 64(6):2240-6 (1998).
Bjarnsholt et al., Interference of Pseudomonas aeruginosa signalling and biofilm formation for infection control, Expert Rev. Mol. Med., 12:e11 (2010).
Bryk et al., Selective killing of nonreplicating mycobacteria, Cell Host Microbe, 3(3):137-45 (2008).
Bryk et al., Triazaspirodimethoxybenzoyls as selective inhibitors of mycobacterial lipoamide dehydrogenase, Biochemistry, 49(8):1616-27 (2010).
Casenghi et al., New approaches to filling the gap in tuberculosis drug discovery, PLoS Med., 4(11):e293 (2007).
Chen et al., Structural identification of a bacterial quorum-sensing signal containing boron, Nature, 415(6871):545-9 (2002).
Chugani et al., QscR, a modulator of quorum-sensing signal synthesis and virulence in Pseudomonas aeruginosa, Proc. Natl. Acad. Sci. USA, 98(5):2752-7 (2001).
Darby et al., Killing of non-replicating *Mycobacterium tuberculosis* by 8-hydroxyquinoline, J. Antimicrob. Chemother., 65(7):1424-7 (2010).
de Carvalho et al., Nitazoxanide kills replicating and nonreplicating *Mycobacterium tuberculosis* and evades resistance, J. Med. Chem., 52(19):5789-92 (2009).
Dekimpe et al., Revisiting the quorum-sensing hierarchy in Pseudomonas aeruginosa: the transcriptional regulator RhlR regulates LasR-specific factors, Microbiology, 155(Pt. 3):712-23 (2009).
Dupuy et al., Free radical heterocyclization of acetylenic thiols, Bulletin de la Societe Chimique de France, 7-8(Pt. 2):361-73 (1980). [French only.].
Fleet et al., Polyhydroxylated pyrrolidines from sugar lactomes: Synthesis of 1,4-dideoxy-1,4-imino-d-glucitol from d-galactonolactone and syntheses of 1,4-dideoxy-1,4-imino-d-allitol, 1,4-dideoxy-1,4-imino-d-ribitol, and (2s,3r,4s)-3,4-dihydroxyproline from d-gulonolactone, Tetrahedron, 44:2637-47 (1988).
Geske et al., Expanding dialogues: from natural autoinducers to non-natural analogues that modulate quorum sensing in Gram-negative bacteria, Chem. Soc. Rev., 37(7):1432-47 (2008).
Geske et al., Modulation of bacterial quorum sensing with synthetic ligands: systematic evaluation of N-acylated homoserine lactones in multiple species and new insights into their mechanisms of action, J. Am. Chem. Soc., 129(44):13613-25 (2007).
Gopishetty et al., Probing the catalytic mechanism of S-ribosylhomocysteinase (LuxS) with catalytic intermediates and substrate analogues, J. Am. Chem. Soc., 131(3):1243-50 (2009).
Graeme Cran et al., Scalemic beta-amino sulfide ligands: use in enantioselective conjugate additions and x-ray analysis of a dimeric copper(I) complex, Tetrahedron: Asymmetry, 7(9):251 1-4 (1996).
Graeme Cran et al., Synthesis of chiral beta-amino sulfides and beta-amino thiols from alpha-amino acids, Tetrahedron: Asymmetry, 6(7):1553-6 (1995).

(Continued)

*Primary Examiner* — Robert Havlin
(74) *Attorney, Agent, or Firm* — Marshall, Gerstein & Borun LLP

(57) ABSTRACT

Compounds of Formula (I) are disclosed herein and their use in inhibiting quorum sensing in bacteria.

15 Claims, 2 Drawing Sheets

(56) References Cited

OTHER PUBLICATIONS

Haidle et al., An enantioselective, modular, and general route to the cytochalasins: synthesis of L-696,474 and cytochalasin B, Proc. Natl. Acad. Sci. USA, 101 (33):12048-53 (2004).
Hentzer et al., Inhibition of quorum sensing in Pseudomonas aeruginosa biofilm bacteria by a halogenated furanone compound, Microbiology, 148(Pt.1):87-102 (2002).
Higuchi et al., Pro-drugs as Novel Delivery Systems, vol. 14 of the American Chemical Society Symposium Series.
Hu et al., Structure of the *Mycobacterium tuberculosis* proteasome and mechanism of inhibition by a peptidyl boronate, Mol. Microbiol., 59(5):1417-28 (2006).
International Preliminary Report on Patentability, International Application No. PCT/US12/042899, dated Dec. 17, 2013.
International Search Report and Written Opinion, International application No. PCT/US2012/042899, mailing date Sep. 7, 2012.
Ishida et al., Inhibition of quorum sensing in Pseudomonas aeruginosa by N-acyl cyclopentylamides, Appl. Environ. Microbiol., 73(10):3183-8 (2007).
Kline et al., Substituted 2-imino-5-arylidenethiazolidin-4-one inhibitors of bacterial type III secretion, J. Med. Chem., 51(22):7065-74 (2008).
Lee et al., Activity of purified QscR, a Pseudomonas aeruginosa orphan quorum-sensing transcription factor, Mol. Microbiol., 59(2):602-9 (2006).
Lin et al., Fellutamide B is a potent inhibitor of the *Mycobacterium tuberculosis* proteasome, Arch. Biochem. Biophys., 501(2):214-20 (2010).
Lin et al., Inhibitors selective for mycobacterial versus human proteasomes, Nature, 461(7264):621-6 (2009).
Magolda et al., Design and synthesis of conformationally restricted phospholipids as phospholipase A2 inhibitors, J. Cell Biochem., 40(3):371-86 (1989).
Malladi et al., Substituted lactam and cyclic azahemiacetals modulate Pseudomonas aeruginosa quorum sensing, Bioorg. Med. Chem., 19(18):5500-6 (2011).
Manefield et al., Halogenated furanones inhibit quorum sensing through accelerated LuxR turnover, Microbiology, 148(Pt. 4):1119-27 (2002).
Maricic et al., Inhibition of quorum sensing in Pseudomonas aeruginosa and Vibrio harveyi using synthesized 4-AZA S-ribosyl homocystein analogues, Cold Spring Harbor Laboratory Meeting on Microbial Pathogenesis and Host Response (Sep. 8-12, 2009).
Mathee et al., Identification of a positive regulator of the Mu middle operon, J. Bacteriol., 172(12):6641-50 (1990).
Miller, Experiments in Molecular Genetics, Cold Spring Habor Laboratory (1972).
Morohoshi et al., Inhibition of quorum sensing in Serratia marcescens AS-1 by synthetic analogs of N-acylhomoserine lactone, Appl. Environ. Microbiol., 73(20):6339-44 (2007).
Muh et al., Novel Pseudomonas aeruginosa quorum-sensing inhibitors identified in an ultrahigh-throughput screen, Antimicrob. Agents Chemother., 50(11):3674-9 (2006).
Murruzzu et al., Enantioselective synthesis of hydroxylated pyrrolidines via Sharpless epoxidation and olefin metathesis, Tetrahedron: Asymmetry, 18:149-54 (2007).
Nathan et al., A philosophy of anti-infectives as a guide in the search for new drugs for tuberculosis, Tuberculosis (Edinb), 88 (Suppl 1):S25-33 (2008).
Ng et al., Bacterial quorum-sensing network architectures, Annu. Rev. Genet., 43:197-222 (2009).
Nicolaides et al., Modified di- and tripeptides of the C-terminal portion of oxytocin and vasopressin as possible cognition activation agents, J. Med. Chem., 29(6):959-71 (1986).
Otsuka et al., Synthetic studies on antitumor antibiotic, bleomycin. 27. Man-designed bleomycin with altered sequence specificity in DNA cleavage, J. Am. Chem. Soc., 112:838-45 (1990).
Passador et al., Functional analysis of the Pseudomonas aeruginosa autoinducer PAI, J. Bacteriol., 178(20):5995-6000 (1996).
Pearson et al., Active efflux and diffusion are involved in transport of Pseudomonas aeruginosa cell-to-cell signals, J. Bacteriol., 181(4):1203-10 (1999).
Pearson et al., Roles of Pseudomonas aeruginosa las and rhl quorum-sensing systems in control of elastase and rhamnolipid biosynthesis genes, J. Bacteriol., 179(18):5756-67 (1997).
Qiu et al., Synthesis of 3'-deoxy-3'-difluoromethyl azanucleosides from trans-4-hydroxy-l-proline, J. Org. Chem., 70(10):3826-37 (2005).
Raffa et al., Bacterial communication ("quorum sensing") via ligands and receptors: a novel pharmacologic target for the design of antibiotic drugs, J. Pharmacol. Exp. Ther., 312(2):417-23 (2005).
Roche (ed.), Bioreversible Carriers in Drug Design, American Pharmaceutical Association and Pergamon Press (1987).
Schaefer et al., Quorum sensing in Vibrio fischeri: probing autoinducer-LuxR interactions with autoinducer analogs, J. Bacteriol., 178(10):2897-901 (1996).
Smith et al., IL-8 production in human lung fibroblasts and epithelial cells activated by the Pseudomonas autoinducer N-3-oxododecanoyl homoserine lactone is transcriptionally regulated by NF-kappa B and activator protein-2, J. Immunol., 167(1):366-74 (2001).
Smith et al., Induction and inhibition of Pseudomonas aeruginosa quorum sensing by synthetic autoinducer analogs, Chem. Biol., 10(1):81-9 (2003).
Telford et al., The Pseudomonas aeruginosa quorum-sensing signal molecule N-(3-oxododecanoyl)-L-homoserine lactone has immunomodulatory activity, Infect. Immun., 66(1):36-42 (1998).
Waldmann et al., Chemoenzymatic synthesis of fluorescent N-Ras lipopeptides and their use in membrane localization studies in vivo, Angew. Chem. Int. Ed. English., 36(20):2238-41 (1997).
Watson et al., Heterogeneously catalyzed asymmetric hydrogenation of C=C bonds directed by surface-tethered chiral modifiers, J. Am. Chem. Soc., 131:14584-9 (2009).
Williams et al., Quorum sensing and environmental adaptation in Pseudomonas aeruginosa: a tale of regulatory networks and multifunctional signal molecules, Curr. Opin. Microbiol., 12(2):182-91 (2009).
Witte et al., Synthesis of a potent [alpha]-glucosidase inhibitor epimeric to FR 900483, Tetrahedron Lett., 32:3927-30 (1991).
Wnuk et al., Inhibition of S-ribosylhomocysteinase (LuxS) by substrate analogues modified at the ribosyl C-3 position, Bioorg. Med. Chem., 17(18):6699-706 (2009).
Wu et al., Detection of N-acylhomoserine lactones in lung tissues of mice infected with Pseudomonas aeruginosa, Microbiology, 146(Pt. 10):2481-93 (2000).

\* cited by examiner

2-METHYLTHIOPYRROLIDINES AND THEIR USE FOR MODULATING BACTERIAL QUORUM SENSING

CROSS-REFERENCE TO RELATED APPLICATIONS

The benefit under 35 U.S.C. §119(e) of U.S. Provisional Patent Application No. 61/497,811, filed Jun. 16, 2011, is hereby claimed, the disclosure of which is incorporated by reference in its entirety.

STATEMENT OF U.S. GOVERNMENT INTEREST

This invention was made with U.S. government support under grant number SC1CA138176 awarded by the National Institutes of Health. The government has certain rights in the invention.

BACKGROUND

Quorum sensing (QS) is a type of bacterial cell-to-cell signaling pathway mediated through the production, release and detection of the small signaling molecules called autoinducers (AIs) (reviewed in (1)). Such communication allows bacterial control of crucial functions in united communities for enhancement of symbiosis, virulence, antibiotic production, biofilm formation, and many other processes. The recent increase in prevalence of bacterial strains resistant to antibiotics emphasizes the need for the development of a new generation of antibacterial agents. As QS is utilized by number of pathogenic bacteria to direct virulence and biofilm formation, inhibitors/modulators of QS may serve as tools to study or intercept such community behaviors and might be beneficial as antibacterial agents (2). One of the chemical signals, or autoinducers (AIs) used by Gram-negative bacteria are acyl homoserine lactones (AHLs), which are detected by their cognate regulator (R) proteins (1).

The QS system *Vibrio fischeri* (recently reclassified as *Aliivibrio fisheri*) serves as the paradigm upon which all other QS systems are based. It is composed of a transcriptional regulator protein (R) and a synthetase (I). The R protein is unstable unless it binds to the AHL which is produced by the synthetase. *V. fischeri* produces N-3-(oxo-hexanoyl)-homoserine lactone (3OC6HSL), *V. harveyi* synthesizes N-3-hydroxybutanoil-homoserine lactone (HAI-1), and *Pseudomonas aeruginosa* produces two distinct AHLs: N-3-oxo-dodecanoyl-L-homoserine lactone (3-OC12-HSL) and N-butyryl-L-homoserine lactone (C4-HSL). *V. harveyi* produces a second signalling molecule, a furnosyl borate diester, termed autoinducer-2 (AI-2), and a third CAI-1. CAI-1 has been identified in *V. cholerae* to be (s)-3 hydroxytridecan-4-one. *P. aeruginosa* also has a third QS signaling molecule, 2-heptyl-3-hydroxy-4-quinolone (PQS), which is induced and repressed by the las and rhl systems, respectively.

*Pseudomonas aeruginosa* is an important human opportunistic pathogen affecting immunocompromised individuals, cancer patients, burn victims, cystic fibrosis patients and patients with impaired lung function. It uses two AHL systems called, las and rhl to mediate QS. LasI/R synthesizes and detects N-(3-oxo-dodecanoyl)-L-homoserine lactone (3-oxo-C12-AHL) while RhlI/R synthesizes and detects N-butanoyl-L-homoserine lactone (C4-AHL) (FIG. 1a). In addition, *P. aeruginosa* has a third QS-dependent pathway, *Pseudomonas quinolone* signal (PQS) that uses 2-heptyl-3-hydroxy-4-quinolone as an autoinducer (reviewed in (3)). Although, certain genes appear to be regulated by one pathway, for example regulation of genes involved in rhamnolipid synthesis by the rhl pathway (4), there is much overlap between the pathways and what was once thought to be a hierarchical pathway, with las activating rhl, is now known to be much more complex (5). Accumulated evidences clearly indicate the importance of *P. aeruginosa* QS in disease (6).

Over two decades, several small molecules have been identified by many research groups as inhibitors of the AHL:R protein complex. These are mostly AHL-based structures with moderate changes on the acyl side chain and amide linkage. Some of the most potent inhibitors prepared by Geske and Blackwell are shown in FIG. 1b (7). Recently, Meijler and co-workers designed a ligand, 3, which covalently modified LasR (8). Since AHL is the pharmacophore present in the natural substrates, AHL-based inhibitors are likely to modulate R protein activation.

Studies of structural features other than the AHL scaffold as tools to understand the R type protein interaction with AHLs are limited, although they might aid in rational design of QS inhibitors. Only a few examples of inhibitors with the altered lactone ring structure of AHL have been reported (9-12). For example, Smith et al reported 3-oxo-C12-(2-aminocyclohexanone) (FIG. 1c, 4) as a strong antagonist of LasR system (9), while Muh et al identified two LasR inhibitors having a phenyl and stetrazole ring (e.g. FIG. 1c, 5), with IC50 in nM range (FIG. 1c) (10). It is noteworthy that γ-thiolactone analogue of 1 (FIG. 1b) showed inhibition of LuxR while the corresponding ε-lactam (caprolactam) analogue was reported to lack LuxR binding (13). Thus, a need exists for new QS inhibitors.

SUMMARY

Disclosed herein are compounds of formula (I):

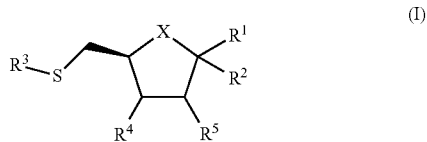

wherein $R^1$ and $R^2$ are each independently H or OH, or $R^1$ and $R^2$ taken together are oxo; $R^3$ is $C_2$-$C_{20}$alkyl, $C_1$-$C_{20}$alkyleneCO$_2$H, $C_1$-$C_{20}$alkyleneCO$_2$—$C_1$-$C_6$alkyl or $C_1$-$C_{20}$alkylene-amino; $R^4$ and $R^5$ are each independently H or OH, or $R^4$ and $R^5$ taken together with the carbons that they are attached form a 4-7 membered cyclic or heterocyclic ring; X is $NR^6$ or S; and $R^6$ is H or C(O)alkyl; or a salt or ester thereof. In various embodiments, $R^1$ is OH and $R^2$ is H. In various cases, $R^1$ and $R^2$ together are oxo. In various cases, at least one of $R^4$ and $R^5$ is OH. In some cases, both $R^4$ and $R^5$ are OH. In various cases, both $R^4$ and $R^5$ are H. In various cases, X is S. In various cases, X is $NR^6$. In various cases, $R^6$ is H. In various cases, $R^6$ is C(O)alkyl. In various cases, $R^3$ is $C_3$-$C_{12}$alkyl. In various cases, $R^3$ is $C_1$-$C_{20}$alkyleneCO$_2$H. In various cases, $R^3$ is $C_1$-$C_{20}$alkyleneCO$_2$—$C_1$-$C_6$alkyl. In various cases, $R^3$ is $C_1$-$C_{20}$alkyleneCO$_2$-amino. In various cases, the compound of formula (I) has a structure selected from

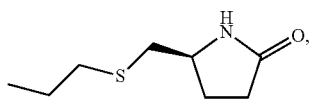

-continued

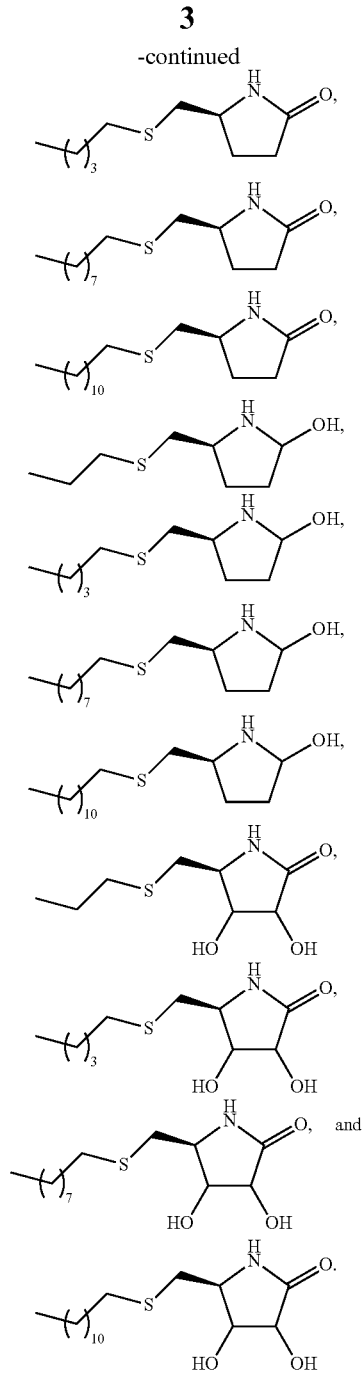

Further provided herein are methods of inhibiting bacterial quorum sensing comprising contacting bacteria with a compound as disclosed herein, or a compound as disclosed herein formulated in a composition. In some cases, the bacteria are selected from Acinetobacter baumannii, Aeromonas hydrophila, Aeromonas salmonicida, Agrobacterium tumefaciens, Brucella melitensis, Burkholderia cenocepacia, Burkholderia mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas aeruginosa, Pseudomonas fluorescens, Pseudomonas fuscovaginae, Pseudomonas syringae, Ralstonia solanacearum, Rhizobium etli, Rhizobium leguminosarum, Rhodobacter sphaeroides, Serratia liquefaciens, Serratia marcescens, Vibrio anguillarum, Vibrio fischeri, Vibrio parahaemolyticus, Vibrio salmonicida, Xanthomonas campestris, Xenorhabdus nematophilus, Yersinia enterocolitica, Yersinia pestis, Yersinia pseudotuberculosis, Yersinia medievalis, Yersinia ruckeri, and combinations thereof. In various cases, the contacting comprises administering to a subject suffering from a bacterial infection. In some cases, the subject is human. In some cases, the subject is an animal.

Further contemplated is administering a second agent to the subject, such as an antibiotic agent. Specific antibiotic agents contemplated include a penicillin, a selexcid, a cephalosporin, a tetracycline, a rifamycin, gentamycin, clindamycin, a fluoroquinolone, a monobactamer, a carbapeneme, a macrolide, a polymyxin, an aminoglycoside, tobramycin, a sulfonamide, a fusidine, a vancomycin, an oxazolidinone, a metronidazole, a corticosteroid, hydrocortisone, triamcinolone, betamethasone, and combinations thereof. The second agent and the compound of formula (I) can be administered sequentially or at the same time. In some cases, the second agent is administered before the compound of formula (I), while in other cases, the second agent is administered after the compound of formula (I). In some cases, the second agent and the compound of formula (I) are co-formulated.

Further provided herein are methods of treating a subject suffering from a bacterial infection comprising administering a compound as disclosed herein, or a compound as disclosed herein formulated in a composition. Also contemplated is further administering a second agent as disclosed herein, e.g., an antibiotic. In some cases, the infection is a P. aeruginosa infection.

Also provided herein are methods of inhibiting biofilm formation comprising contacting bacteria with a compound as disclosed herein, or a compound as disclosed herein formulated in a composition.

DETAILED DESCRIPTION

Figure 1:
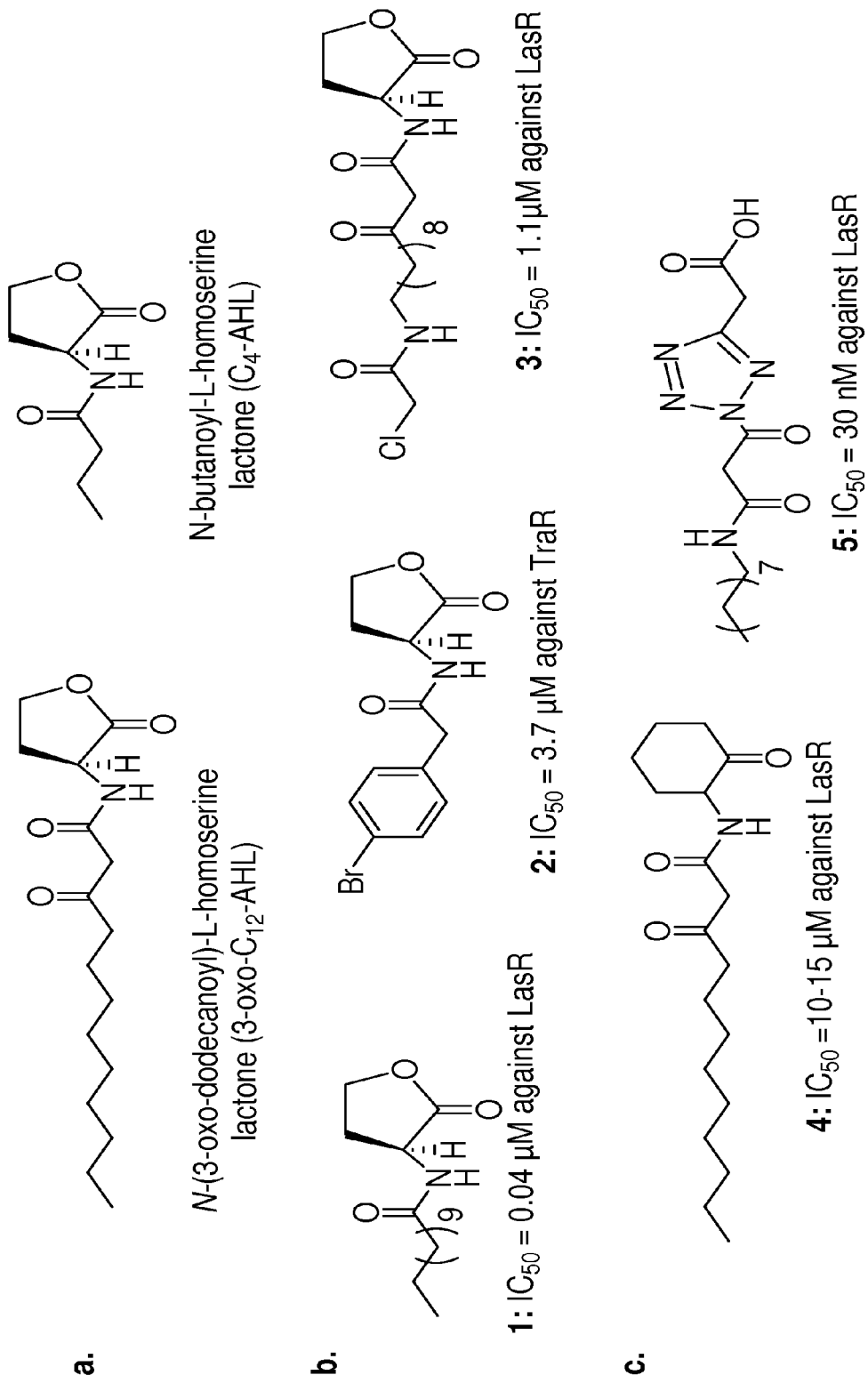
FIG. 1 shows (a) AHL based signal molecules in P. aeruginosa. (b) Examples of most potent synthetic QS inhibitors in various Gram-negative bacteria along with their reported $IC_{50}$ values (7-8). (c) Examples of QS inhibitors with alteration of AHL scaffold (9-10).

QS has been known to regulate a variety of cellular functions in many pathogenic bacteria including Pseudomonas aeruginosa. The QS machinery, including the two in P. aeruginosa, LasI/R and RhlI/R, are based on the Vibrio harveyi paradigm which includes a synthetase (I) and a regulator protein (R). The signaling molecule synthesized in Gram negative bacteria is acyl homoserine lactone (AHL) which activates QS. In addition, V. harveyi uses another signaling molecule, autoinducer II (AI-2), which is structurally different from AHLs, to activate bioluminescence. However, both bacteria use similar intermediates in synthesizing these signaling molecules, S-ribosylhomocysteine (SRH) and S-adenosyl-homocysteine (SAH) in V. harveyi and P. aeruginosa, respectively. Since it is known that QS deficient strains are less pathogenic, alternative treatments that target the QS system are being explored.

To explore further effects of non-native AHL scaffold on QS, novel lactam ligands were designed. Here, optically pure γ-lactams and cyclic azahemiacetals, bearing alkylthiomethyl substituent with different length of carbon chain (C3-C12) are reported, which are capable of either inhibiting or, in some cases, inducing QS in *P. aeruginosa*. The lactam ring was chosen because it is a more stable isoster of lactone ring present in AHL inhibitors. Moreover, the γ-lactam and cyclic azahemiacetal ligands were further modified in a such way that they resemble S-ribosyl-L-homocysteine, which is known to regulate QS through the LuxS-mediated biosynthesis of AI-2 (1, 14-16), in which the ribose oxygen is replaced with a nitrogen atom and the homocysteine unit is substituted with a simple alkylthiol chain. Described herein are analogs of SRH and SAH and their effect on *V. harveyi* and *P. aeruginosa* as determined by luminescence and a β-galactosidase assays. In particular, disclosed herein are compounds of formula (I):

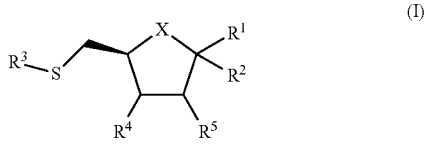

wherein $R^1$ and $R^2$ are each independently H or OH, or $R^1$ and $R^2$ taken together are oxo; $R^3$ is $C_2$-$C_{20}$alkyl, $C_1$-$C_{20}$alkyleneCO$_2$H, $C_1$-$C_{20}$alkyleneCO$_2$—$C_1$-$C_6$alkyl or $C_1$-$C_{20}$alkylene-amino; $R^4$ and $R^5$ are each independently H or OH, or $R^4$ and $R^5$ taken together with the carbons that they are attached form a 4-7 membered cyclic or heterocyclic ring; X is $NR^6$ or S; and $R^6$ is H or C(O)alkyl; or a salt or ester thereof. In some cases, $R^1$ is OH and $R^2$ is H. In some cases, $R^1$ and $R^2$ taken together are oxo. In some cases, at least one of $R^4$ and $R^5$ is OH. In some cases, $R^4$ and $R^5$ are each OH. In some cases, $R^4$ and $R^5$ are each H. In some cases, X is S. In some cases, X is $NR^6$. In some cases, $R^6$ is H. In some cases, $R^6$ is C(O)alkyl. In some cases, $R^3$ is $C_3$-$C_{12}$alkyl. In some cases, $R^3$ is $C_6$-$C_{12}$alkyl. In some cases, $R^3$ is $C_1$-$C_{20}$alkyleneCO$_2$H. In some cases, $R^3$ is $C_1$-$C_{20}$alkyleneCO$_2$—$C_1$-$C_6$alkyl. In some cases, $R^3$ is $C_1$-$C_{20}$alkyleneCO$_2$-amino.

The term "alkyl" used herein refers to a saturated or unsaturated straight or branched chain hydrocarbon group, including, but not limited to, methyl, ethyl, n-propyl, isopropyl, n-butyl, isobutyl, tert-butyl, n-hexyl, and the like. Alkyls of one to six carbon atoms, three to twenty, three to twelve, four to twenty, four to twelve, five to twenty, five to twelve, six to twenty, six to twelve, seven to twenty, seven to twelve, eight to twenty, eight to twelve, nine to twenty, nine to twelve, and ten to twenty are also contemplated. The term "alkyl" includes "bridged alkyl," i.e., a bicyclic or polycyclic hydrocarbon group, for example, norbornyl, adamantyl, bicyclo [2.2.2]octyl, bicyclo[2.2.1]heptyl, bicyclo[3.2.1]octyl, or decahydronaphthyl. Alkyl groups optionally can be substituted, for example, with hydroxy (OH), halide, thiol (SH), aryl, heteroaryl, cycloalkyl, heterocycloalkyl, and amino.

As used herein, the term "cycloalkyl" refers to a cyclic hydrocarbon group, e.g., cyclopropyl, cyclobutyl, cyclohexyl, and cyclopentyl. "Heterocycloalkyl" is defined similarly as cycloalkyl, except the ring contains one to three heteroatoms independently selected from the group consisting of oxygen, nitrogen, and sulfur. Nonlimiting examples of heterocycloalkyl groups include piperidine, tetrahydrofuran, tetrahydropyran, dihydrofuran, morpholine, thiophene, and the like. Cycloalkyl and heterocycloalkyl groups can be saturated or partially unsaturated ring systems optionally substituted with, for example, one to three groups, independently selected from the group consisting of alkyl, alkyleneOH, C(O)NH$_2$, NH$_2$, oxo (=O), aryl, haloalkyl, halo, and OH. Heterocycloalkyl groups optionally can be further N-substituted with alkyl, hydroxyalkyl, alkylenearyl, or alkyleneheteroaryl.

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four groups independently selected from, for example, halo, alkyl, alkenyl, OCF$_3$, NO$_2$, CN, NC, OH, alkoxy, amino, CO$_2$H, CO$_2$alkyl, aryl, and heteroaryl. Exemplary aryl groups include, but are not limited to, phenyl, naphthyl, tetrahydronaphthyl, chlorophenyl, methylphenyl, methoxyphenyl, trifluoromethylphenyl, nitrophenyl, 2,4-methoxychlorophenyl, and the like.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, OCF$_3$, NO$_2$, CN, NC, OH, alkoxy, amino, CO$_2$H, CO$_2$alkyl, aryl, and heteroaryl. In some cases, the heteroaryl group is substituted with one or more of alkyl and alkoxy groups. Examples of heteroaryl groups include, but are not limited to, thienyl, furyl, pyridyl, oxazolyl, quinolyl, thiophenyl, isoquinolyl, indolyl, triazinyl, triazolyl, isothiazolyl, isoxazolyl, imidazolyl, benzothiazolyl, pyrazinyl, pyrimidinyl, thiazolyl, and thiadiazolyl.

As used herein the term "amino" refers to a —NR$_2$ group, where each R is independently hydrogen or alkyl, e.g., —NH$_2$, —NH(alkyl), or —N(alkyl)$_2$. When the amino is substituted with two alkyl groups, the alkyl groups can be the same (e.g., —NMe$_2$) or different (e.g., —N(Me)(iPr)).

Of the analogs tested, four demonstrated anti-QS activity (S-[2-Oxopyrrolidin-5-yl)methyl)]thiopropanol [5-(Propylthiomethyl)pyrrolidin-2-one] (OMPP), S-[2-Oxopyrrolidin-5-yl)methyl)]thiopropanol [5-Hexylthiomethyl)pyrrolidin-2-one] (OMHP), S—[N-Benzyl-3,4-dihyroxy-2-oxopyrrolidin-5-yl)methyl]-L-homocysteine (BDOH), and S-[2-Hydroxypyrrolidin-5-yl)methyl]thiopropanol[5-Propylthiomethyl)-2-hydroxy-pyrrolidin] (HMPP)). BDOH and HMPP exhibited a strong anti-QS effect against *V. harveyi*. OMPP and OMHP had a dosed dependent inhibition on the expression of the lasI promoter of *P. aeruginosa*. The data presented herein demonstrates that the analogs described herein can be used to interrupt bacterial communication in difference bacteria and would be useful as an effective treatment for bacterial infections.

Compounds disclosed herein show selectivity between two QS systems, acting as inhibitors against las signaling and moderate activators against rhl signaling, possibly due to differences in the active sites of their cognate R proteins or transport of the native signaling molecule. Antagonism of las activity increased with the length of the alkylthio chain. Interestingly, the cyclic azahemiacetal derivatives with shorter alkylthio chain were found to stimulate both QS systems at lower concentrations while strongly inhibiting at higher concentrations. The ribolactam and the corresponding cyclic azahemiacetal analogues inhibited las and stimulated rhl moderately. Although, the mechanism of inhibition is still unknown, it is plausible that the compounds act as competitive inhibitors by binding to the QS sensor or affect events downstream, such as the binding of lasR (or in some cases, rhlR) to the promoter. Affecting downstream events would require that the compound enter the cells, which is unknown. Alternatively, it is established that although the rhl signaling molecule, $C_4$-AHL diffuses freely, transport of the las signaling molecule is more complex, involving partitioning into the membrane and transport out of the cell by the MexAB-OprM efflux pump (27). Thus, it is also possible that the compounds with longer side chains affect the membrane and that the las pathway is more sensitive to these changes. Given the central role the las and rhl QS pathways play in *P. aeruginosa* virulence, inhibitors such as the ones described here, have significant potential as therapeutics.

Specific compounds of formula (I) contemplated include:

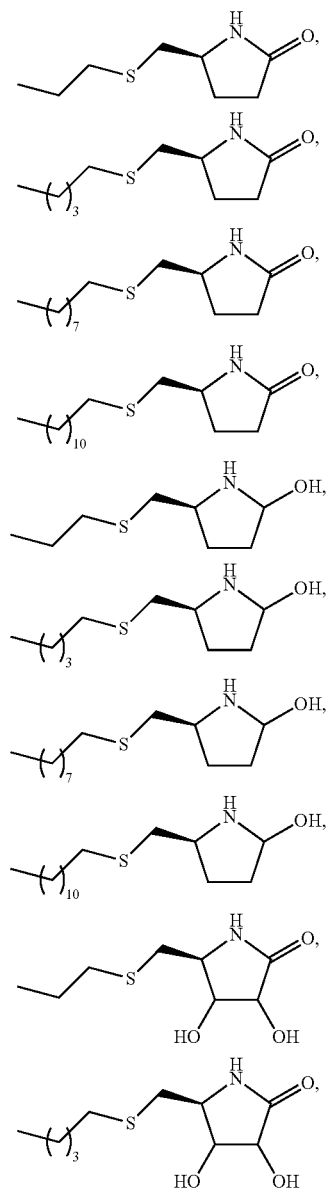

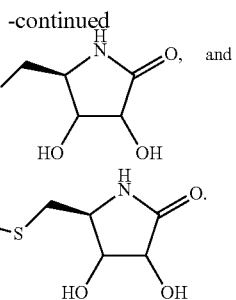

Asymmetric carbon atoms can be present. All such isomers, including diastereomers and enantiomers, as well as the mixtures thereof, are intended to be included in the scope of the disclosure herein. In certain cases, compounds can exist in tautomeric forms. All tautomeric forms are intended to be included in the scope of the disclosure herein. Likewise, when compounds contain an alkenyl or alkenylene group, there exists the possibility of cis- and trans-isomeric forms of the compounds. Both cis- and trans-isomers, as well as the mixtures of cis- and trans-isomers, are contemplated.

The salts, e.g., pharmaceutically acceptable salts, of the disclosed therapeutics may be prepared by reacting the appropriate base or acid with a stoichiometric equivalent of the therapeutic.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, O-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

Pharmaceutically acceptable base addition salts may be formed with metals or amines, such as alkali and alkaline earth metals or organic amines. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible. Examples of metals used as cations are sodium, potassium, magnesium, ammonium, calcium, or ferric, and the like. Examples of suitable amines include isopropylamine, trimethylamine, histidine, N,N'-dibenzylethylenediamine, chloroprocaine, choline, diethanolamine, dicyclohexylamine, ethylenediamine, N-methylglucamine, and procaine.

Similarly, pharmaceutically acceptable derivatives (e.g., esters), metabolites, hydrates, solvates and prodrugs of the therapeutic may be prepared by methods generally known to those skilled in the art. Thus, another embodiment provides compounds that are prodrugs of an active compound. In general, a prodrug is a compound which is metabolized in vivo (e.g., by a metabolic transformation such as deamination, dealkylation, de-esterification, and the like) to provide an active compound. A "pharmaceutically acceptable prodrug" means a compound which is, within the scope of sound medical judgment, suitable for pharmaceutical use in a patient without undue toxicity, irritation, allergic response, and the like, and effective for the intended use, including a pharmaceutically acceptable ester as well as a zwitterionic form, where possible, of the therapeutic. As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Representative examples of particular esters include, but are not limited to, formates, acetates, propionates, butyrates, acrylates and ethylsuccinates. Examples of pharmaceutically-acceptable prodrug types are described in Higuchi and Stella, *Prodrugs as Novel Delivery Systems*, Vol. 14 of the A.C.S. Symposium Series, and in Roche, ed., *Bioreversible Carriers in Drug Design*, American Pharmaceutical Association and Pergamon Press, 1987, both of which are incorporated herein by reference.

The compounds and compositions described herein may also include metabolites. As used herein, the term "metabolite" means a product of metabolism of a compound of the embodiments or a pharmaceutically acceptable salt, analog, or derivative thereof, that exhibits a similar activity in vitro or in vivo to a disclosed therapeutic. The compounds and compositions described herein may also include hydrates and solvates. As used herein, the term "solvate" refers to a complex formed by a solute (herein, the therapeutic) and a solvent. Such solvents for the purpose of the embodiments preferably should not negatively interfere with the biological activity of the solute. Solvents may be, by way of example, water, ethanol, or acetic acid.

Pharmaceutical Compositions

The terms "therapeutically effective amount" and "prophylactically effective amount," as used herein, refer to an amount of a compound sufficient to treat, ameliorate, or prevent the identified disease or condition, or to exhibit a detectable therapeutic, prophylactic, or inhibitory effect. The effect can be detected by, for example, an improvement in clinical condition, reduction in symptoms, or by any of the assays or clinical diagnostic tests described herein. The precise effective amount for a subject will depend upon the subject's body weight, size, and health; the nature and extent of the condition; and the therapeutic or combination of therapeutics selected for administration. Therapeutically and prophylactically effective amounts for a given situation can be determined by routine experimentation that is within the skill and judgment of the clinician.

Dosages of the therapeutic can alternately be administered as a dose measured in mg/kg. Contemplated mg/kg doses of the disclosed therapeutics include about 0.001 mg/kg to about 1000 mg/kg. Specific ranges of doses in mg/kg include about 0.1 mg/kg to about 500 mg/kg, about 0.5 mg/kg to about 200 mg/kg, about 1 mg/kg to about 100 mg/kg, about 2 mg/kg to about 50 mg/kg, and about 5 mg/kg to about 30 mg/kg.

As herein, the compounds described herein may be formulated in pharmaceutical compositions with a pharmaceutically acceptable excipient, carrier, or diluent. The compound or composition comprising the compound is administered by any route that permits treatment of the disease or condition. One route of administration is oral administration. Additionally, the compound or composition comprising the compound may be delivered to a patient using any standard route of administration, including parenterally, such as intravenously, intraperitoneally, intrapulmonary, subcutaneously or intramuscularly, intrathecally, topically, transdermally, rectally, orally, nasally or by inhalation. Slow release formulations may also be prepared from the agents described herein in order to achieve a controlled release of the active agent in contact with the body fluids in the gastro intestinal tract, and to provide a substantial constant and effective level of the active agent in the blood plasma. The crystal form may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

Administration may take the form of single dose administration, or a compound as disclosed herein can be administered over a period of time, either in divided doses or in a continuous-release formulation or administration method (e.g., a pump). However the compounds of the embodiments are administered to the subject, the amounts of compound administered and the route of administration chosen should be selected to permit efficacious treatment of the disease condition.

In an embodiment, the pharmaceutical compositions are formulated with one or more pharmaceutically acceptable excipient, such as carriers, solvents, stabilizers, adjuvants, diluents, etc., depending upon the particular mode of administration and dosage form. The pharmaceutical compositions should generally be formulated to achieve a physiologically compatible pH, and may range from a pH of about 3 to a pH of about 11, preferably about pH 3 to about pH 7, depending on the formulation and route of administration. In alternative embodiments, the pH is adjusted to a range from about pH 5.0 to about pH 8. More particularly, the pharmaceutical compositions may comprise a therapeutically or prophylactically effective amount of at least one compound as described herein, together with one or more pharmaceutically acceptable excipients. Optionally, the pharmaceutical compositions may comprise a combination of the compounds described herein, or may include a second active ingredient useful in the treatment or prevention of bacterial infection (e.g., anti-bacterial or anti-microbial agents.

Formulations, e.g., for parenteral or oral administration, are most typically solids, liquid solutions, emulsions or suspensions, while inhalable formulations for pulmonary administration are generally liquids or powders. A pharmaceutical composition can also be formulated as a lyophilized solid that is reconstituted with a physiologically compatible solvent prior to administration. Alternative pharmaceutical compositions may be formulated as syrups, creams, ointments, tablets, and the like.

The term "pharmaceutically acceptable excipient" refers to an excipient for administration of a pharmaceutical agent, such as the compounds described herein. The term refers to any pharmaceutical excipient that may be administered without undue toxicity.

Pharmaceutically acceptable excipients are determined in part by the particular composition being administered, as well as by the particular method used to administer the composition. Accordingly, there exists a wide variety of suitable formulations of pharmaceutical compositions (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants (e.g., ascorbic acid), chelating agents (e.g., EDTA), carbohydrates (e.g., dextrin, hydroxyalkylcellulose, and/or hydroxyalkylmethylcellulose), stearic acid, liquids (e.g., oils, water, saline, glycerol and/or ethanol) wetting or emulsifying agents, pH buffering substances, and the like. Liposomes are also included within the definition of pharmaceutically acceptable excipients.

The pharmaceutical compositions described herein are formulated in any form suitable for an intended method of administration. When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients particularly suitable for use in conjunction with tablets include, for example, inert diluents, such as celluloses, calcium or sodium carbonate, lactose, calcium or sodium phosphate; disintegrating agents, such as cross-linked povidone, maize starch, or alginic acid; binding agents, such as povidone, starch, gelatin or acacia; and lubricating agents, such as magnesium stearate, stearic acid or talc.

Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules wherein the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In another embodiment, pharmaceutical compositions may be formulated as suspensions comprising a compound of the embodiments in admixture with at least one pharmaceutically acceptable excipient suitable for the manufacture of a suspension.

In yet another embodiment, pharmaceutical compositions may be formulated as dispersible powders and granules suitable for preparation of a suspension by the addition of suitable excipients.

Excipients suitable for use in connection with suspensions include suspending agents (e.g., sodium carboxymethylcellulose, methylcellulose, hydroxypropyl methylcellulose, sodium alginate, polyvinylpyrrolidone, gum tragacanth, gum acacia); dispersing or wetting agents (e.g., a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monoleate)); and thickening agents (e.g., carbomer, beeswax, hard paraffin or cetyl alcohol). The suspensions may also contain one or more preservatives (e.g., acetic acid, methyl or n-propyl p-hydroxy-benzoate); one or more coloring agents; one or more flavoring agents; and one or more sweetening agents such as sucrose or saccharin.

The pharmaceutical compositions may also be in the form of oil-in water emulsions. The oily phase may be a vegetable oil, such as olive oil or arachis oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monoleate; and condensation products of these partial esters with ethylene oxide, such as polyoxyethylene sorbitan monoleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions may be in the form of a sterile injectable preparation, such as a sterile injectable aqueous emulsion or oleaginous suspension. This emulsion or suspension may be formulated by a person of ordinary skill in the art using those suitable dispersing or wetting agents and suspending agents, including those mentioned above. The sterile injectable preparation may also be a sterile injectable solution or suspension in a non-toxic parenterally acceptable diluent or solvent, such as a solution in 1,2-propane-diol.

The sterile injectable preparation may also be prepared as a lyophilized powder. Among the acceptable vehicles and solvents that may be employed are water, Ringer's solution, and isotonic sodium chloride solution. In addition, sterile fixed oils may be employed as a solvent or suspending medium. For this purpose any bland fixed oil may be employed including synthetic mono- or diglycerides. In addition, fatty acids (e.g., oleic acid) may likewise be used in the preparation of injectables.

To obtain a stable water-soluble dose form of a pharmaceutical composition, a pharmaceutically acceptable salt of a compound described herein may be dissolved in an aqueous solution of an organic or inorganic acid, such as 0.3 M solution of succinic acid, or more preferably, citric acid. If a soluble salt form is not available, the compound may be dissolved in a suitable co-solvent or combination of co-solvents. Examples of suitable co-solvents include alcohol, propylene glycol, polyethylene glycol 300, polysorbate 80, glycerin and the like in concentrations ranging from about 0 to about 60% of the total volume. In one embodiment, the active compound is dissolved in DMSO and diluted with water.

The pharmaceutical composition may also be in the form of a solution of a salt form of the active ingredient in an appropriate aqueous vehicle, such as water or isotonic saline or dextrose solution. Also contemplated are compounds which have been modified by substitutions or additions of chemical or biochemical moieties which make them more suitable for delivery (e.g., increase solubility, bioactivity, palatability, decrease adverse reactions, etc.), for example by esterification, glycosylation, PEGylation, etc.

In some embodiments, the compounds described herein may be formulated for oral administration in a lipid-based formulation suitable for low solubility compounds. Lipid-based formulations can generally enhance the oral bioavailability of such compounds.

As such, pharmaceutical compositions comprise a therapeutically or prophylactically effective amount of a compound described herein, together with at least one pharmaceutically acceptable excipient selected from the group consisting of medium chain fatty acids and propylene glycol esters thereof (e.g., propylene glycol esters of edible fatty acids, such as caprylic and capric fatty acids) and pharmaceutically acceptable surfactants, such as polyoxyl 40 hydrogenated castor oil.

In some embodiments, cyclodextrins may be added as aqueous solubility enhancers. Exemplary cyclodextrins include hydroxypropyl, hydroxyethyl, glucosyl, maltosyl and maltotriosyl derivatives of α-, β-, and γ-cyclodextrin. A specific cyclodextrin solubility enhancer is hydroxypropyl-o-cyclodextrin (BPBC), which may be added to any of the above-described compositions to further improve the aqueous solubility characteristics of the compounds of the embodiments. In one embodiment, the composition comprises about 0.1% to about 20% hydroxypropyl-o-cyclodextrin, more preferably about 1% to about 15% hydroxypropyl-o-cyclodextrin, and even more preferably from about 2.5% to about 10% hydroxypropyl-o-cyclodextrin. The amount of solubility enhancer employed will depend on the amount of the compound of the invention in the composition.

Quorum Sensing

Some bacteria have a system by which they can monitor the density of their own population and control the expression of specific genes only when a certain population density has been reached. This ability to monitor cell density has been found in more than 20 different bacterial species, and has been termed quorum sensing. Pathogenic bacteria use quorum sensing to turn on virulence pathways and form drug-impervious communities called biofilms that are the basis of a myriad chronic infections. Over 80% of bacterial infections in humans involve the formation of biofilms, as exemplified in lung infections by Pseudomonas aeruginosa, which is the primary cause of morbidity in cystic fibrosis patients.

The existence of quorum sensing was established in the early 1970s where experiments showed that bioluminescence of the bacterium Vibrio fischeri is a function of cell density, and that it is controlled by a small diffusible molecule, later identified to be a N-acyl-homoserine lactone (AHL), namely N-(3-oxohexanoyl)-L-homoserine lactone.

The quorum sensing system of V. fischeri serves well as a basis for describing and understanding quorum sensing systems. It comprises a signal molecule synthase (LuxI) which produces the signal molecule (AHL, in casu N-(oxo-hexanoyl)-L-homoserine lactone) from a precursor, and a signal molecule dependent receptor protein (LuxR). When the concentration of the signal molecule reaches a threshold level, i.e. when the population of the bacterium reaches a certain level, the signal molecule interacts with the receptor protein to effect an activation of it. The LuxR-AHL complex binds to the lux box in the promoter region of the gene, which, in turn, initiates the transcription of luxI (the gene encoding LuxI) and other genes responsible for bioluminescence. The LuxI production thus generates a positive autoregulatory loop. The signal molecules are often referred to as autoinducers.

Many Gram-negative bacteria have been shown to posses one or more quorum sensing systems homologues to the LuxR/LuxI system just described for V. fischeri, and Pseudomonas aeruginosa in particular appears to have at least two quorum sensing systems, i.e. las and rhl. The las system comprises a signal molecule generating synthase (LasI), the major product of which is N-(3-oxo-dodecanoyl)-homoserine lactone (OdDHL), and a receptor protein LasR. The rhl system comprises a signal generating synthase (RhlI), the major product of which is N-butyryl-homoserine lactone, and a receptor protein RhlI. The las system modulates the expression of LasI, RhlI, LasR and virulence factors, such as elastase, staphylolytic protease, alkaline protease, exotoxin and neuraminidase, and biofilm differentiation. The rhl system modulates the expression of RhlI, rhamnolipid and virulence factors, such as alkaline protease, elastase, haemolysin, pyocyanin and hydrogen cyanide. Moreover, in vitro immunoassays on human leukocytes have shown that OdDHL possesses immunomodulatory properties, e.g. inhibition of lymphocyte proliferation and down-regulation of tumor necrosis factor alpha production and of IL-12 production (Telford et al., Infect. Immun, 66, 36, 1998). In addition, OdDHL has been demonstrated to activate T-cells in vivo to produce the inflammatory cytokine interferon-γ (Smith et al., J. Immunol., 167, 366, 2001) and, thereby, potentially promote a Th2-dominated response leading to increased tissue damage and inflammation.

An important effect of a quorum sensing system is that, e.g. virulence factors are only excreted when the population has reached a certain density. This is probably of vital importance for invading organisms because they, at low density, are more susceptible to the defense systems of the host. If an invading organism unveiled its presence by excreting virulence factors when still at a low population density, they would be more easily targeted by the host's defense mechanisms A quorum sensing system endows bacteria with a capability to reach a critical population density whereby they overwhelm the host's immune defense and establish an infection.

The rationale behind quorum sensing based drugs is multifaceted. By preventing the excretion of virulence factors, the pathogenicity of the invading organism is diminished, or even eliminated. Furthermore, as described above, the signal molecules may themselves have an adverse effect on the immune system of the host, so inhibiting the production of signal molecules will have a beneficial effect. Finally, the development of persistent biofilms in some bacteria, e.g. Pseudomonas aeruginosa is also affected by the quorum sensing system (Hentzer et al., Microbiology 148, 87, 2002). Although the biofilm itself may not be virulent, it protects the invading organism from the defense systems of the host. By preventing the formation of persistent biofilms, the invading organism is left exposed to the defense systems of the host, and the host may thus be able to clear the infection on its own. Alternatively, the infectious organism will be left more receptive to treatment with conventional antibiotics. It is thus envisaged that an embodiment of the invention involving a combination treatment, wherein a quorum sensing inhibitor of the present invention and an antibiotic is administered to a patient will be particular beneficial for certain types of infections.

Inhibiting the quorum sensing system as such will not have a toxic effect on the bacterium, and, while not wishing to be bound by theory, it is believed that this will have an impact on the build-up of resistance towards such drugs. Resistance to antibiotics is generated under the imposition of a selection pressure favoring mutants that are capable of tolerating the toxins. Quorum sensing inhibitors as such can be non-toxic, and they are therefore not expected to impose a selection pressure on the bacteria. As a consequence, the formation of resistant strains is expected to be at a minimum, i.e. the background mutational rate. Toxicity may be quantified in a simple assay wherein the bacterium *Escherichia coli* is left to grow planktonic in the absence or presence of a test compound. Bacterial cultures are grown in ABt minimal medium supplemented with 0.5% casamino acids and 0.5% glucose (referred to as growth medium). The ABt medium contains: $(NH_4)_2SO_4$ (2 g/L), $Na_2HPO_4 \cdot 2H_2O$ (6 g/L), $KH_2PO_4$ (3 g/L), NaCl (3 g/L), $MgCl_2$ (93 mg/L), $CaCl_2$ (11 mg/l), and thiamine (0.5 mg/L). Culture conditions: The 20 ml cultures were grown in 100 ml conical flasks in an orbital air shaker at 200 rpm at 37° C. The cultures are inoculated from overnight cultures in fresh medium at an optical density of approximately $OD_{450}$=0.2. The cultures are grown to $OD_{450}$=1.0, then diluted in fresh test medium to $OD_{450}$=0.2. Growth is monitored by $OD_{450}$ every 5 min. Compounds, which at concentration lower than 10 mM, lower than 1 mM, lower than 500 µM, or lower than 100 µM cause an increase of the doubling time during the exponential growth phase relative to the doubling time in the absence of the compound by more than 5%, e.g. 10%, e.g. more than 30%, such as more than 60%, such as more than 95% are said to be toxic.

The absence of toxicity is also believed to reduce the number of adverse effects. Treatments involving traditional antibiotics are often connected with unpleasant side effect, e.g. diarrhea caused by the effect of the antibiotics on the beneficial bacteria present in the gut. As quorum sensing inhibitors are non-toxic, they are not expected to affect other bacteria than those exploiting a quorum sensing system and the number of adverse effects is thus likely to be reduced.

Different assays are described in the literature by which to assess if a given compound is a quorum sensing inhibitor. WO 00/06177 discloses a method that assesses the extent to which the activity of the signal molecule synthase is modulated by a given test compound. The method provides a labeled homoserine lactone substrate, allows the reaction to proceed to completion and determines the extent of the homoserine lactone substrate to homoserine lactone conversion in the absence and presence of the test compound. Wu, et al., Microbiol 146, 2481, 2000, and Andersen et al., Appl. Envirom. Microbiol., 67, 575, 2001, describe how part of the quorum sensing system, i.e. the luxR and the luxI promoter from *Vibrio fischeri* may be fused with a gene encoding unstable versions (Andersen et al., Appl Environ Microbiol 64, 2240, 1998) of the green fluorescence protein (GFP). This fusion (referred to as the LuxR-QS-monitor) may be incorporated into bacterial strains which, if exposed to a signal molecule, will produce GFP which can be detected by epifluorescence spectroscopy. WO 01/18248 discloses the use of other reporter genes than GFP, e.g. luciferase. The quorum sensing inhibiting effect of a given compound may also be quantified in an assay wherein the lasR and the lasB promoter from *Pseudomonas aeruginosa* fused with the gene encoding unstable GFP (referred to as the LasR-QS-monitor) is incorporated into the chromosome of *Pseudomonas aeruginosa* or a plasmid vehicle as disclosed in Hentzer et al, Microbiol, 148, 87, 2002.

Manefield et al, Microbiology, 148, 1119, 2002, describe a method to scientifically demonstrate and quantify the QSI activity of compounds. *E. coli*, into which the LuxR-QS-monitor was incorporated, was inoculated from an overnight culture in fresh culture medium at a density of approximately $OD_{450}$=1, and incubated at 37° C. for approximately 30 min. Aliquots (200 µl) of this culture were distributed to the wells of microtiter dishes into which a known signal molecule, namely $N$-(3-oxo-hexanoyl)-L-homoserine lactone (OHHL) at 25, 50 and 100 nM, and the test compound had been pipetted. After two hours of incubation at 37° C. the relative fluorescence units (RFU) of each sample were captured with in Wallac Victor2, 1420 Multilabel Counter using a 485 nm excitation filter and a 535 nm emission filter. The RFU values obtained for each concentration were used to calculate an inhibition index expressing the quantity of test compound per quantity of OHHL required to inhibit LuxR controlled $P_{luxI}$-GFP expression to a given level (X %). This is termed the IDX value. The three values obtained, one for each OHHL concentration, were plotted as a function of OHHL concentration and the gradient of the best straight line fitted to the three points and passing through the origin was taken as the inhibition index (IIX). The IIX expresses the number of µmol of test compound per nanomole OHHL required to inhibit expression of fluorescence to X % of the untreated sample. A low IIX value may therefore be interpreted as to reflect a compound with high efficacy. Test compounds with IIX lower than 10, lower than 5, lower than 1, lower than 0.5, lower than 0.1, or lower than 0.05 for X higher than 10%, such as higher than 20%, higher than 40%, higher than 60%, higher than 95% exhibit quorum sensing inhibition.

The assays discussed above use parts of the quorum sensing system from particular bacteria incorporated into particular bacteria. Despite that, it has been found that such reporter systems function in a number of different bacteria, and that they are responsive to a variety of quorum sensing inhibitors (Manefield et al, Microbiology, 148, 1119, 2002). The applied assay is therefore useful to identify compounds which inhibit the quorum sensing system in a wide range of bacteria, e.g. *Pseudomonas aeruginosa*.

Gram-negative bacteria represent numerous relevant pathogens using quorum-sensing pathways. Besides *P. aeruginosa*, other Gram-negative quorum sensing bacteria include: *Acinetobacter baumannii, Aeromonas hydrophila, Aeromonas salmonicida, Agrobacterium tumefaciens, Brucella melitensis, Burkholderia cenocepacia, Burkholderia mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas fluorescens, Pseudomonas fuscovaginae, Pseudomonas syringae, Ralstonia solanacearum, Rhizobium etli, Rhizobium leguminosarum, Rhodobacter sphaeroides Rhodobacter sphaeroides, Serratia liquefaciens, Serratia marcescens, Vibrio anguillarum, Vibrio cholerae, Vibrio fisheri, Vibrio parahaemolyticus, Vibrio salmonicida, Xenorhabdus nematophilus, Yersinia enterocolitica, Yersinia pestis, Yersinia pseudotuberculosis, Yersinia medievalis*, and *Yersinia ruckeri*.

Methods of Treatment

Biofilms are dense extracellular polymeric matrices in which bacteria embed themselves. Biofilms allow bacteria to create a microenvironment that attaches the bacteria to the host surface and which contains excreted enzymes and other factors allowing the bacteria to evade host immune responses including antibodies and cellular immune responses. Such biofilms can also exclude antibiotics. Further, biofilms can be extremely resistant to removal and disinfection. For individuals suffering from cystic fibrosis, the formation of biofilms by *P. aerugniosa* is eventually fatal. Other bacteria also respond to quorum sensing signals by producing biofilms. Biofilms are inherent in dental plaques, and are found on surgical instruments, food processing and agriculture equipment and water treatment and power generating machinery and equipment.

Thus, provided herein is a method of treating a disorder associated with quorum sensing or biofilm formation in a mammalian subject, the method comprising administering a compound of formula (I) as disclosed herein to the subject in an amount effective to disrupt quorum sensing or biofilm formation in the subject. The subject can be human, animal, or plant. In some specific cases, the subject is human. In some specific cases, the subject is an animal. Specifically contemplated animal subjects include fish and amphibians. In some specific cases, the subject is a plant.

In various embodiments, the disorder associated with biofilm formation in the subject is selected from the group consisting of cystic fibrosis, dental caries, periodonitis, otitis media, muscular skeletal infections, necrotizing fasciitis, biliary tract infection, osteomyelitis, bacterial prostatitis, endocarditis, native valve endocarditis, cystic fibrosis pneumonia, meloidosis, or skin lesions associated with bullous impetigo, atopic dermatitis and pemphigus foliaceus or implanted device-related infections. In some embodiments, the condition is a nosocomial infection, including but not limited to, pneumonia or an infection associated with sutures, exit sites, arteriovenous sites, scleral buckles, contact lenses, urinary catheter cystitis, peritoneal dialysis (CAPD) peritonitis, IUDs, endrotracheal tubes, Hickman catheters, central venous catheters, mechanical heart valves, vascular grafts, biliary stent blockage, and orthopedic devices.

Also provided is a method of modulating biofilm formation on a surface, the method comprising contacting the surface with a compound of formula (I) as disclosed herein in an amount effective for disrupt or inhibit biofilm formation on the surface. In one embodiment, the surface is an inanimate surface. Exemplary inanimate surfaces include, but are not limited to, metal, glass, plastic, wood and stone surfaces. In another embodiment, the surface is an animate surface. Exemplary animate surfaces include, but are not limited to, mammalian tissues, mammalian membranes, mammalian skin.

As used herein, the term "pathogenic bacterium" or "pathogenic bacteria" refers to both gram-negative and gram-positive bacterial cells capable of infecting and causing disease in a mammalian host, as well as producing infection-related symptoms in the infected host, such as fever or other signs of inflammation, intestinal symptoms, respiratory symptoms, dehydration, and the like.

In some embodiments, and without limitation, the bacteria is of a genus selected from the group consisting of *Aeromonas, Agrobacterium, Burkholderia, Chromobacterium, Enterobacter, Erwinia, Escherichia, Nitrosomas, Obesumbacterium, Pantoea, Pseudomonas, Ralstonia, Rhisobium, Rhodobacter, Serratia, Staphyllococcus, Vibrio, Xenorhabdus,* and *Yersinia*. For example, in some embodiments and without limitation, the bacteria is of a species selected from the group consisting of: *Acinetobacter baumannii, Aeromonas hydrophila, Aeromonas salmonicida, Agrobacterium tumefaciens, Brucella melitensis, Burkholderia cenocepacia, Burkholderia mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas aeruginosa, Pseudomonas fluorescens, Pseudomonas fuscovaginae, Pseudomonas syringae, Ralstonia solanacearum, Rhizobium etli, Rhizobium leguminosarum, Rhodobacter sphaeroides, Serratia liquefaciens, Serratia marcescens, Vibrio anguillarum, Vibrio fischeri, Vibrio parahaemolyticus, Vibrio salmonicida, Xanthomonas campestris, Xenorhabdus nematophilus, Yersinia enterocolitica, Yersinia pestis, Yersinia pseudotuberculosis, Yersinia medievalis,* and *Yersinia ruckeri*.

Also provided is a method of treating a disorder associated with QS in a mammalian subject resistant to treatment with a standard of care anti-bacterial therapeutic comprising administering to the subject a compound of formula (I) as disclosed herein in an amount effective to inhibit QS in the bacteria causing the infection.

Contemplated bacterial infections include, but are not limited to, bacteremia, septicemia, endo- and pericarditis, sinusitis, wound infection, burn wounds, upper respiratory tract infection, urinary tract infection, gastroenteritis, intra-abdominal infections, arthritis, pseudotuberculosis, chronic bronchitis, pneumonia, cerebral, pulmonary, and skin lesions, cerebral and liver abscesses, meningitis, dermatitis or folliculitis, necrotizing fasciitis, cellulitis, urinary tract infections, Glander's disease, osteomylitis, enterocolitis, contact lens-associated keritis, and conjunctivitis. The treatment may also be used to treat infections immunocompromised individuals, such as those with cancer and acquied immunodeficiency syndrome (AIDS). These compounds may also be useful in treating disorders associated with biofilm formation in patients with cystic fibrosis, dental caries, periodonitis, otititis media, muscular skeletal infections, necrotizing fasciitis, biliary tract infection, osteomyelitis, bacterial prostatitis, endocarditis, native valve eendocarditis, cystic fibrosis pneumonia, infections associated with chronic granulomatous, meloidosis, or skin lesions associated with bullous impetigo, atopic dermatitis and pemphigus foliaceus or implanted device-related infections. It may also be used to treat nosocomial infections including pneumonia, infection associated with sutures, exit sites, arteriovenous sites, scleral buckles, contact lenses, urinary catheter cystitis peritoneal dialysis peritonitis, IUDs, endotracheal tubes, Hickman catheters, central venous catheters, mechanical heart valves, vascular grafts, biliary stent blockage, and orthopedice devices.

Combination Therapy

The methods of the embodiments also include the use of a compound or compounds as described herein together with one or more additional therapeutic agents for the treatment of disease conditions. Thus, for example, the combination of active ingredients may be: (1) co-formulated and administered or delivered simultaneously in a combined formulation; (2) delivered by alternation or in parallel as separate formulations; or (3) by any other combination therapy regimen known in the art. When delivered in alternation therapy, the methods described herein may comprise administering or delivering the active ingredients sequentially, e.g., in separate solution, emulsion, suspension, tablets, pills or capsules, or by different injections in separate syringes. In general, during alternation therapy, an effective dosage of each active ingredient is administered sequentially, i.e., serially, whereas in simultaneous therapy, effective dosages of two or more active ingredients are administered together. Various sequences of intermittent combination therapy may also be used.

In some cases, a compound disclosed herein is administered and/or formulated with a second therapeutic—e.g., an antibacterial agent.

Antibacterial agents contemplated for use include, without limitation, antibiotics of the β-lactam group such as natural penicillins, semisynthetic penicillins, natural cephalosporins, semisynthetic cephalosporins, cephamycins, 1-oxacephems, clavulanic acids, penems, carbapenems, nocardicins, monobactams; tetracyclines, anhydrotetracyclines, anthracyclines; aminoglycosides; nucleosides such as N-nucleosides, C-nucleosides, carbocyclic nucleosides, blasticidin S; macrolides such as 12-membered ring macrolides, 14-membered ring macrolides, 16-membered ring macrolides; ansamycins; peptides such as bleomycins, gramicidins, polymyxins, bacitracins, large ring peptide antibiotics containing lactone linkages, actinomycins, amphomycin, capreomycin, distamycin, enduracidins, mikamycin, neocarzinostatin, stendomycin, viomycin, virginiamycin; cycloheximide; cycloserine; variotin; sarkomycin A; novobiocin; griseofulvin; chloramphenicol; mitomycins; fumagillin; monensins; pyrroInitrin; fosfomycin; fusidic acid; D-(p-hydroxyphenyl)glycine; D-phenylglycine; enediynes; benzylpenicillin (potassium, procaine, benzathine), phenoxymethylpenicillin (potassium), phenethicillin potassium, propicillin, carbenicillin (disodium, phenyl sodium, indanyl sodium), sulbenicillin, ticarcillin disodium, methicillin sodium, oxacillin sodium, cloxacillin sodium, dicloxacillin, flucloxacillin, ampicillin, mezlocillin, piperacillin sodium, amoxicillin, ciclacillin, hectacillin, sulbactam sodium, talampicillin hydrochloride, bacampicillin hydrochloride, pivmecillinam, cephalexin, cefaclor, cephaloglycin, cefadroxil, cephradine, cefroxadine, cephapirin sodium, cephalothin sodium, cephacetrile sodium, cefsulodin sodium, cephaloridine, cefatrizine, cefoperazone sodium, cefamandole, vefotiam hydrochloride, cefazolin sodium, ceftizoxime sodium, cefotaxime sodium, cefinenoxime hydrochloride, cefuroxime, ceftriaxone sodium, ceftazidime, cefoxitin, cefinetazole, cefotetan, latamoxef, clavulanic acid, imipenem, aztreonam, tetracycline, chlortetracycline hydrochloride, demethylchlortetracycline, oxytetracycline, methacycline, doxycycline, rolitetracycline, minocycline, daunorubicin hydrochloride, doxorubicin, aclarubicin, kanamycin sulfate, bekanamycin, tobramycin, gentamycin sulfate, dibekacin, amikacin, micronomicin, ribostamycin, neomycin sulfate, paromomycin sulfate, streptomycin sulfate, dihydrostreptomycin, destomycin A, hygromycin B, apramycin, sisomicin, netilmicin sulfate, spectinomycin hydrochloride, astromicin sulfate, validamycin, kasugamycin, polyoxin, blasticidin S, erythromycin, erythromycin estolate, oleandomycin phosphate, tracetyloleandomycin, kitasamycin, josamycin, spiramycin, tylosin, ivermectin, midecamycin, bleomycin sulfate, peplomycin sulfate, gramicidin S, polymyxin B, bacitracin, colistin sulfate, colistinmethanesulfonate sodium, enramycin, mikamycin, virginiamycin, capreomycin sulfate, viomycin, enviomycin, vancomycin, actinomycin D, neocarzinostatin, bestatin, pepstatin, monensin, lasalocid, salinomycin, amphotericin B, nystatin, natamycin, trichomycin, mithramycin, lincomycin, clindamycin, clindamycin palmitate hydrochloride, flavophospholipol, cycloserine, pecilocin, griseofulvin, chloramphenicol, chloramphenicol palmitate, mitomycin C, pyrroInitrin, fosfomycin, fusidic acid, bicozamycin, tiamulin, or siccanin. In some cases, the second therapeutic agent blocks virulence products. In such cases, the bacteria is prevented from secreting its virulence factors (toxins etc.) and the immune system can clear the bacteria. See, e.g., Lin et al., *Arch Biochem Biophys*. 2010 Sep. 15; 501(2):214-20. Epub 2010 Jun. 15; Darby et al., *J Antimicrob Chemother*. 2010 July; 65(7):1424-7. Epub 2010 Apr. 30; Bryk et al, *Biochemistry*. 2010 Mar. 2; 49(8):1616-27; Lin et al., *Nature*. 2009 Oct. 1; 461(7264):621-6. Epub 2009 Sep. 16; de Carvalho et al., *J Med. Chem*. 2009 Oct. 8; 52(19):5789-92; Nathan et al., *Tuberculosis* (Edinb). 2008 August; 88 Suppl 1:S25-33; Bryk, et al., *Cell Host Microbe*. 2008 Mar. 13; 3(3):137-45; Casenghi, et al., *PLoS Med*. 2007 Nov. 6; 4(11):e293; Hu et al., *Mol. Microbiol*. 2006 March; 59(5):1417-28; and Kline et al., *J Med. Chem*. 2008 Nov. 27; 51(22):7065-74.

Further contemplated are antibacterial agents selected from acedisulfone, aceturate, acetyl sulfametossipirazine, acetyl sulfamethoxypyrazine, acranil, albendazole, alexidine, amatadine, ambazone, amdinocillin, amikacin, p-aminosalicyclic acid hydrazine, amoxicillin, ampicillin, anisomycin, apalcillin, apicyclin, apramycin, arbekacin, argininsa, aspoxicillin, azidamfenicol, azidocillin, azithromycin, azlocillin, aztreonam, bacampicillin, benzoylpas, benzyl penicillin acid, benzyl sulfamide, bicozamycin, bipenam, brodimoprim, capreomycin, carbenicillin, carbomycin, cafazedone, carindacillin, carumonam, cefcapene pivoxil, cefaclor, cefazedone, cefazolin, cefbuperazone, cefclidin, cefdinir, cefditoren, cefixime, cefinenoxime, cefinetazole, cefminox, cefodizime, cefonicid, cefoperazone, ceforanide, cefotaxime, cefotetan, cefotiam, cefoxitin, cefozopran, cefpimizole, cefpriamide, cefpirome, cefpodoxime proxetil, cefprozil, cefroxadine, cefsulodin, ceftazidime, cefteram, ceftezole, ceftibuten, ceftiofur, ceftizoxime, ceftriaxone, cefuroxime, cefuzonam, cephacetrile sodium, cephadrine, cephalexin, cephaloglycin, cephaloridine, cephalosporin C, cephalothin, cephapirin sodium, cephradine, chloramphenicol, chlorotetracycline, cinoxacin, ciprofloxacin, clarithromycin, clavulanic acid, clinafloxacin, clindamycin, clofazimine, clofoctal, clometocillin, clomocycline, cloxacillin, cloxyquin, cyclacilline, cycloserine, danoflaxcin, dapsone, deoxycycline, deoxydihydrostreptomycin, dibekacin, dicloxacillin, difloxacin, dihydrostreptomycin, dimetridazole, diminazene, dirirtomycin, doripenam, eflornithine, enoxacin, enrofloxacin, enviomycin, epicillin, erythromycin, etacillin, ethambutol, ethionamide, famciclovir, fenbecillin, fleroxacin, flomoxef, floxacillin, flumequine, furonazide, fortimycin, furazolium chloride, gentamycin, glyconiazide, grepafloxacin, guamecycline, halofuginone, hetacillin, homidium, ipronidazole, isoniazide, iosamycin, inosine, lauroguadine, lenampicillin, levofloxin, lincomycin, lomefloxacin, loracarbef, lymecyclin, mafenide, mebendazole, meclocyclin, meropenem, metampicillin, metacicline, methacycline, methicillin sodium, metronidazole, 4'-(methylsulfamoyl) sulfanilanilide, mezlocillin, meziocillin, micronomycin, midecamycin $A_1$, minocycline, miocamycin, miokamycin, morfazinamide, moxalactam, mupirocin, myxin, nadifloxacin, nalidixic acid, negramycin, neomycin, netlimycin, nifurfoline, nifurpirinol, nifurprazine, nimorazole, nitroxoline, norfloxacin, novobiocin, ofloxacin, oleandomycin, opiniazide, oxacillin, oxophenarsine, oxolinic acid, oxytetracycline, panipenam, paromycin, pazufloxacin, pefloxacin, penicillin G potassium salt, penicillin N, penicillin O, penicillin V, penethamate hydroiodide, pentamidine, phenamidine, phenethicillin potassium salt, phenyl aminosalicyclate, pipacycline, pipemidic acid, piperacillin, pirlimycin, piromidic acid, pivampicillin, pivcefalexin, profiromycin, propamidine, propicillin, protionamide, puraltadone, puromycin, pyrazinamide, pyrimethamine, quinacillin, quinacrine, quinapyramine, quintine, ribostamycin, rifabutine, rifamide, rifampin, rifamycin, rifanpin, rifapentine, rifaxymine, ritipenem, rokitamycin, rolitetracycline, rosamycin, rufloxacin, salazosulfadimidine, salinazid, sancycline, sarafloxacin, sedacamycin, secnidazole, sisomycin, sparfloxacin, spectinomycin, spiramycin, spiramycin I, spiramycin II, spiramycin III, stilbamidine, streptomycin, streptonicizid, sulbactam, sulbenicillin, succisulfone, sulfanilamide, sulfabenzamide, sulfacetamide, sulfachloropyridazine, sulfachrysoidine, sulfacytine, sulfadiazine, sulfadicramide, sulfadimethoxin, sulfadoxine, sulfadrazine, sulfaetidol, sulfafenazol, sulfaguanidine, sulfaguanole, sulfalene, sulfamerazine, sulfameter, sulfamethazine, sulfamethizole, sulfamethomidine, sulfamethoxazole, sulfamethoxypyridazine, sulfamethylthiazol, sulfamethylthiazole, sulfametrole, sulfamidochrysoidine, sulfamoxole, sulfanilamide, 4-sulfanilamido salicylic acid, 4-4'-sulfanilylbenzylamine, p-sulfanilylbenzylamine, 2-p-sulfinylanilinoethanol, sulfanilylurea, sulfoniazide, sulfaperine, sulfaphenazole, sulfaproxyline, sulfapyrazine, sulfapyridine, sulfathiazole, sulfaethidole, sulfathiourea, sulfisomidine, sulfasomizole, sulfasymazine, sulfisoxazole, 4,4'-sulfinyldianiline, $N^4$-sulfanilylsulfanilamide, N-sulfanilyl-3,4-xylamide, sultamicillin, talampicillin, tambutol, taurolidine, teiclplanin, temocillin, tetracycline, tetroxoprim, thiabendazole, thiazolsulfone, tibezonium iodide, ticarcillin, tigemonam, tinidazole, tobramycin, tosufloxacin, trimethoprim, troleandromycin, trospectomycin, trovafloxacin, tubercidine, miokamycin, oleandomycin, troleandromycin, vancomycin, verazide, viomycin, virginiamycin, and zalcitabine.

The invention will be more fully understood by reference to the following examples which detail exemplary embodiments of the invention. They should not, however, be construed as limiting the scope of the invention. All citations throughout the disclosure are hereby expressly incorporated by reference.

EXAMPLES

Example 1

Materials and Methods 5-(Propylthiomethyl)pyrrolidin-2-one [7a(5S)]. Procedure A. Propanethiol (50 µL, 42 mg, 0.55 mmol) was added dropwise to a stirred suspension of NaH (35 mg, 0.875 mmol, 60%/mineral oil) in dry DMF (1 mL) under Ar atmosphere at 0° C. After 10 min (till gas evolution has ceased), solution of compound 6 (17) [(5S), 82 mg, 0.46 mmol] in dry DMF (1 mL) was added dropwise, and after 15 min the reaction mixture was allowed to warm to ambient temperature. After 12 h the resulting mixture was quenched with water at 0° C., volatiles were evaporated, and the residue was column chromatographed (EtOAc→10% MeOH/EtOAc) to give 7a(5S) (77 mg, 96%) as a colorless oil: $^1$H NMR δ 0.98 (t, J=7.3 Hz, 3H), 1.60 (sx, J=7.3 Hz, 2H), 1.76-1.87 (m, 1H), 2.25-2.34 (m, 1H), 2.34-2.45 (m, 2H), 2.52 (t, J=7.3 Hz, 2H), 2.54 (dd, J=7.7, 13.2 Hz, 1H), 2.68 (dd, J=5.5, 13.2 Hz, 1H), 3.80 ('quint', J=5.5 Hz, 1H), 6.73 (br. s, 1H); $^{13}$C NMR δ 13.4, 23.1, 26.6, 30.2, 34.7, 38.6, 53.9, 178.0; MS (APCI) m/z 174 (MH$^+$). HRMS (AP-ESI) m/z calcd for $C_8H_{15}NNaOS$ [M+Na]$^+$ 196.0772; found 196.0779.

N-tert-Butoxycarbonyl-5-(propylthiomethyl)pyrrolidin-2-one [8a(5S)]. Procedure B. DMAP (114 mg, 0.93 mmol), and (Boc)$_2$O (398 mg, 1.82 mmol) were added to a stirred solution of compound 7a (77 mg, 0.445 mmol) in CH$_2$Cl$_2$ (2 mL) at ambient temperature under Ar atmosphere. After 48 h, the reaction mixture was quenched with H$_2$O (5 mL) and partitioned between CH$_2$Cl$_2$//NaHCO$_3$/H$_2$O. The organic layer was washed (brine), dried (MgSO$_4$) and evaporated. The residue was column chromatographed (30→40% EtOAc/hexane) to give 8a (5S) (107 mg, 88%) as a colorless oil: $^1$H NMR δ 0.95 (t, J=7.3 Hz, 3H), 1.50 (s, 9H), 1.58 (sx, J=7.3 Hz, 2H), 1.96-2.04 (m, 1H), 2.06-2.17 (m, 1H), 2.40 (ddd, J=2.6, 9.6, 17.9 Hz, 1H), 2.50 ("dt", J=4.9, 7.3 Hz, 2H), 2.58-2.67 (m, 1H), 2.60 (dd, J=9.2, 13.5 Hz, 1H), 2.86 (dd, J=0.5, 2.8, 13.5 Hz, 1H), 4.20-4.27 (m, 1H); $^{13}$C NMR δ 13.3, 21.9, 23.1, 28.0, 31.2, 34.8, 35.4, 57.5, 83.1, 149.8, 174.2; MS (ESI) m/z 274 (10, MH$^+$), 215 (100, [MH-59]$^+$).

5-(Propylthiomethyl)pyrrolidin-2-ol[10a(5S)]. Procedure C. LiEt$_3$BH (1M soln in THF, 0.98 mL, 0.98 mmol) was added to a stirred solution of 8a (107 mg, 0.39 mmol) in CH$_2$Cl$_2$ (3 mL) at −78° C. under N$_2$ atmosphere. After 30 min, the reaction mixture was quenched with MeOH (4 mL) and was allowed to warm to ambient temperature. Volatiles were evaporated and the residue was partitioned (EtOAc// NaHCO$_3$/H$_2$O), washed (brine) and dried (MgSO$_4$). The resulting oil was chromatographed (30→40% EtOAc/hexane) to give N-tert-butoxycarbonyl-5-(propylthiomethyl)pyrrolidin-2-ol[9a(5S); 104 mg, 96%] as a colorless oil of the mixture of anomers/rotamers: MS (ESI) m/z 274 (10, [M−1]$^+$), 258 (100, [M−17]$^+$). Procedure D. Compound 9a (104 mg, 0.37 mmol) in TFA (4.0 mL) was stirred at rt for 2 h. Volatiles were evaporated to give 10a (62 mg, 96%) as a light yellow oil of a mixture of isomers accompanied by ~25% of the open aldehyde form [$^1$H NMR δ 8.89 (s, ~0.25H); and $^{13}$C NMR δ 180.8]; MS (ESI) m/z 158 (100, [M−17]$^+$).

Structure of compound 10a was additionally confirmed by conversion to the corresponding O-benzyloxime derivative with benzylhydroxylamine hydrochloride (6 equiv.) in anhydrous pyridine: MS (ESI) m/z 281 (60, MH$^+$), 158 (100, [M-BnONH]$^+$), (APCI) m/z 281 (100, MH$^+$).

N-(tert-Butoxycarbonyl)-3,4-dihydroxy-3,4-O-isopropylidene-5-[(methanesulfonyloxy)methyl]pyrrolidin-2-one [13 (3R,4R,5R)]. Step a. Triethylamine (93 µL, mg, 67 mg, 0.66 mmol) and MsCl (25 µL, 38 mg, 0.33 mmol) were added dropwise to stirred solution of 11 (20) (60 mg, 0.22 mmole) in anhydrous CH$_2$Cl$_2$ (6 mL) at 0° C. (ice-bath). After 5 min, ice-bath was removed and the reaction mixture was allowed to stir at ambient temperature for 30 min. The reaction mixture was quenched with saturated NaHCO$_3$/H$_2$O and was extracted with CH$_2$Cl$_2$. The organic layer was washed (brine), dried (MgSO$_4$) and evaporated to give N-tert-butoxycarbonyl-1,4-dideoxy-1,4-imino-2,3-O-isopropylidene-5-O-methanesulfonyl-D-ribitol 12 (73 mg, 96%) as a mixture (~3:2) of two rotamers of sufficient purity to be directly used for next step (see SI for spectral data). Step b. RuO$_2$×H$_2$O (8.5 mg, 0.064 mmol) was added to a stirred solution of NaIO$_4$ (172 mg, 0.96 mmol) in H$_2$O (1 mL) at ambient temperature. After 5 min, a solution of 12 (80 mg, 0.32 mmol) in EtOAc (1 mL) was added dropwise and the reaction mixture was continued to stir for 12 h. H$_2$O (20 mL) and EtOAc (20 mL) were added and the separated aqueous layer was furthermore extracted with EtOAc (2×20 mL). The combined organic layers were washed (brine), dried (MgSO$_4$) and evaporated. The residue was column chromatographed (EtOAc) to give 13 (78 mg, 95%) as a colorless oil: $^1$H NMR δ 1.37 (s, 3H), 1.44 (s, 3H), 1.54 (s, 9H), 3.01 (s, 3H), 4.39-4.43 ('m', 2H), 4.58 (d, J=5.45 Hz, 1H), 4.64 (dd, J=11.2, 3.1 Hz, 1H), 4.70 (d, J=5.45 Hz, 1H); $^{13}$C NMR δ 25.6, 27.0, 28.0, 37.7, 59.2, 67.0, 74.5, 77.5, 84.7, 112.8, 149.7, 170.2; MS (APCI) m/z 298 (100, [MH$_2$−Boc+MeOH]$^+$).

N-(tert-Butoxycarbonyl)-3,4-dihydroxy-3,4-O-isopropylidene-5-(hexylthiomethyl)pyrrolidin-2-one [14 (3R,4R, 5S)]. Treatment of 13 (60 mg, 0.16 mmol) in dry DMF (0.5 mL) with sodium hexathiolate [generated from hexanethiol (46.8 µL, 0.33 mmol)/NaH (14 mg, 0.35 mmol, 60%/mineral oil) in dry DMF (0.5 mL)] by Procedure A [column chromatography (5%→10% MeOH/EtOAc)] gave 14 (25 mg, 40%) as a colorless oil and N-Boc deprotected 14 (24 mg, 38%) as a white crystalline solid. Compound 14 had: $^1$H NMR δ 0.81 (t, J=7.0 Hz, 3H), 1.16-1.27 (m, 6H), 1.30 (s, 3H), 1.39 (s, 3H), 1.44-1.59 (m, 11H), 2.36-2.50 (m, 2H), 2.76 (dd, J=6.2, 14.4 Hz, 1H), 2.82 (dd, J=2.7, 14.4 Hz, 1H), 4.31 (dd, J=2.7, 6.2 Hz, 1H), 4.38 (d, J=5.5 Hz, 1H), 4.78 (d, J=5.5 Hz, 1H);

$^{13}$C NMR δ 14.0, 22.5, 25.5, 27.0, 28.0, 28.3, 29.6, 31.3, 33.7, 33.9, 60.8, 76.1, 77.6, 83.9, 112.3, 149.8, 171.0; MS (APCI) m/z 288 (100, [MH$_2$-Boc]$^+$). N-Boc deprotected 14 had: $^1$H NMR δ 0.88 (t, J=7.0 Hz, 3H), 1.25-1.36 (m, 6H), 1.38 (s, 3H), 1.48 (s, 3H), 1.56-1.62 (m, 2H), 2.52-2.75 (m, 3H), 2.73 (dd, J=5.9, 13.4 Hz, 1H), 3.81 ('t', J=6.1 Hz, 1H), 4.50 (d, J=5.9 Hz, 1H), 4.69 (d, J=5.9 Hz, 1H), 5.94 (s, 1H); $^{13}$C NMR δ 14.0, 29.7, 22.5, 28.5, 31.4, 25.6, 26.9, 33.2, 33.7, 58.0, 76.6, 79.2, 112.7, 173.2; MS (APCI) m/z 288 (100, MH$^+$).

3,4-Dihydroxy-5-(hexylthiomethyl)pyrrolidin-2-one [16 (3R,4R,5S)]. TFA/H$_2$O (1 mL, 9:1) was added to 14 or N-Boc deprotected 14 (22 mg, 0.07 mmol) and the resulting solution was stirred at 0° C. for 3 h. Evaporation of volatiles gave light yellow oil that was column chromatographed (5→10% MeOH/EtOAc) to give 16 (12 mg, 63%) as a colorless oil: $^1$H NMR δ 0.87 (t, J=7.0 Hz, 3H), 1.24-1.39 (m, 6H), 1.52-1.59 (m, 2H), 2.50-2.55 (m, 3H), 2.73 (dd, J=5.5, 13.6 Hz, 1H), 3.71 ('t', J=6.4 Hz, 1H), 4.21 (d, J=5.0 Hz, 1H), 4.44 (d, J=5.0 Hz, 1H), 7.11 (s, 1H); $^{13}$C NMR δ 14.0, 29.6, 14.1, 22.5, 31.4, 32.7, 35.3, 59.9, 69.8, 71.8, 176.0; MS (APCI) m/z 248 (100, MH$^+$).

3,4-Dihydroxy-5-(hexylthiomethyl)pyrrolidin-2-ol[20 (3R,4R,5S)]. Treatment of 14 (40 mg, 0.1 mmol) in THF (1 mL) with LiEt$_3$BH (1M/THF, 0.26 mL, 0.26 mmol), by procedure C [column chromatography (10→20% EtOAc/hexane)] gave N-(tert-butoxycarbonyl)-3,4-dihydroxy-3,4-O-isopropylidene-5-(hexylthiomethyl)pyrrolidin-2-ol[18 (3R,4R,5S)]; 39 mg, 97%)] as a colorless oil of the mixture of isomers: MS (ESI) m/z 389 (100, M$^+$). Deprotection of 18 (39 mg, 0.1 mmol) with TFA/H$_2$O (0.9:0.1 mL) by Procedure D gave a light yellow oil that was column chromatographed (5→10% MeOH/EtOAc) to give 20 (22 mg, 88%) as a light yellow oil. $^1$H NMR showed a mixture of isomers accompanied by the open aldehyde form. MS (APCI) m/z 230 (40, MH$^+$), 232 (100, [M−17]$^+$).

Synthetic procedures and characterization data for compounds 7b-d, 8b-d, 10b-d, 12, 15, 17, and 21 is as follows:

5-(Hexylthiomethyl)pyrrolidin-2-one [7b(5S)]. Treatment of 6 (17) [(5S), 823 mg, 4.62 mmol] in dry DMF (6 mL) with a thiolate solution in dry DMF (6 mL) generated from hexanethiol (682 μL, 573 mg, 4.86 mmol), and NaH (204 mg, 5.09 mmol, 60%/mineral oil) by Procedure A [column chromatography (80% EtOAc/hexane→5% MeOH/EtOAc)] gave 7b(5S) (932 mg, 94%) as a colorless oil: $^1$H NMR δ 0.90 (t, J=7.0 Hz, 3H), 1.24-1.33 (m, 4H), 1.33-1.42 (m, 2H), 1.58 ('quint', J=7.4 Hz, 2H), 1.78-1.87 (m, 1H), 2.27-2.46 (m, 3H) 2.53 (dd, J=8.0, 13.4 Hz, 1H), 2.54 (t, J=7.3 Hz, 2H), 2.70 (dd, J=5.3, 13.2 Hz, 1H), 3.81 ('quint', J=6.6 Hz, 1H), 6.47 (br. s, 1H); $^{13}$C NMR δ 14.0, 22.5, 26.8, 28.5, 29.7, 30.1, 31.4, 32.7, 38.7, 53.8, 177.7; MS (ESI) m/z 216 (100, M$^+$).

5-(Nonylthiomethyl)pyrrolidin-2-one [7c(5S)]. Treatment of 6 (17) [(5S), 458 mg, 2.58 mmol] in dry DMF (3 mL) with thiolate solution in dry DMF (7 mL) generated from nonanethiol (510 μL, 433 mg, 2.71 mmol), and NaH (114 mg, 2.84 mmol, 60%/mineral oil) in dry DMF (7 mL) by Procedure A [column chromatography (80% EtOAc/hexane→EtOAc)] gave 7c(5S) (652 mg, 98%) as a colorless oil: $^1$H NMR δ 0.86 (t, J=7.0 Hz, 3H), 1.19-1.29 (m, 10H), 1.29-1.38 (m, 2H), 1.54 ('quint', J=7.3 Hz, 2H), 1.75-1.85 (m, 1H), 2.23-2.43 (m, 3H), 2.51 (t, J=7.5 Hz, 2H), 2.54 (dd, J=7.4, 13.2 Hz, 1H), 2.65 (dd, J=5.8, 13.2 Hz, 1H), 3.78 ('quint', J=6.5 Hz, 1H), 6.97 (br. s, 1H); $^{13}$C NMR δ 14.1, 22.6, 26.6, 28.8, 29.2, 29.2, 29.4, 29.8, 30.1, 31.8, 32.7, 38.6, 53.9, 178.0; MS (ESI) m/z 258 (100, M$^+$).

5-(Dodecylthiomethyl)pyrrolidin-2-one [7d(5S)]. Treatment of 6 (17) [(5S), 448 mg, 2.52 mmol] in dry DMF (3 mL) with thiolate soln in dry DMF (7 mL) generated from dodecanethiol (634 μL, 535 mg, 2.65 mmol), and NaH (110 mg, 2.77 mmol, 60%/mineral oil) in dry DMF (7 mL) by Procedure A [column chromatography (80% EtOAc/hexane→EtOAc)] gave 7d (5S) (637 mg, 85%) as a colorless oil: $^1$H NMR δ 0.88 (t, J=7.0 Hz, 3H), 1.21-1.32 (m, 16H), 1.32-1.40 (m, 2H), 1.57 ('quint', J=7.4 Hz, 2H), 1.77-1.87 (m, 1H), 2.26-2.45 (m, 3H), 2.53 (t, J=7.6 Hz, 2H), 2.54 (dd, J=7.8, 13.2 Hz, 1H), 2.68 (dd, J=5.4, 13.2 Hz, 1H), 3.80 ('quint', J=6.6 Hz, 1H), 6.64 (br. s, 1H); $^{13}$C NMR δ 14.1, 22.7, 26.7, 28.8, 29.2, 29.3, 29.5, 29.6, 29.6, 29.6, 29.8, 30.1, 31.9, 32.7, 38.7, 53.8, 177.7; MS (ESI) m/z 300 (100, MH$^+$).

N-tert-Butoxycarbonyl-5-(hexylthiomethyl)pyrrolidin-2-one [8b(5S)]. Treatment of 7b (311 mg, 1.45 mmol) in CH$_2$Cl$_2$ (6 mL) with DMAP (185 mg, 1.52 mmol), and (Boc)$_2$O (746 mg, 3.42 mmol) by procedure B [column chromatography (20→40% EtOAc/hexane)] gave 8b (5S) (429 mg, 94%) as a colorless oil: $^1$H NMR δ 0.89 (t, J=7.0 Hz, 3H), 1.25-1.33 (m, 4H), 1.34-1.42 (m, 2H), 1.55 (s, 9H), 1.59 ('quint', J=7.4 Hz, 2H), 2.01-2.08 (m, 1H), 2.10-2.21 (m, 1H), 2.45 (ddd, J=2.5, 9.6, 17.9 Hz, 1H), 2.56 ('dt', J=2.9, 7.3 Hz, 2H), 2.62-2.72 (m, 1H), 2.63 (dd, J=9.3, 13.5 Hz, 1H), 2.91 (dd, J=2.7, 13.5 Hz, 1H), 4.24-4.31 (m, 1H); $^{13}$C NMR δ 14.0, 22.0, 22.5, 28.1, 28.4, 29.8, 31.2, 31.4, 32.9, 35.5, 57.5, 83.1, 149.8, 174.1; MS (ESI) m/z 315 (15, M$^+$), 256 (100, [M−59]$^+$).

N-tert-Butoxycarbonyl-5-(nonylthiomethyl)pyrrolidin-2-one [8c(5S)]. Treatment of 7c (250 mg, 0.97 mmol) in CH$_2$Cl$_2$ (5 mL) with DMAP (125 mg, 1.02 mmol), and (Boc)$_2$O (712 mg, 3.27 mmol) by procedure B [column chromatography (20→25% EtOAc/hexane)] gave 8c(5S) (345 mg, 99%) as a colorless oil: $^1$H NMR δ 0.85 (t, J=7.0 Hz, 3H), 1.19-1.29 (m, 10H), 1.29-1.38 (m, 2H), 1.51 (s, 9H), 1.55 ('quint', J=7.3 Hz, 2H), 1.96-2.04 (m, 1H), 2.06-2.17 (m, 1H), 2.40 (ddd, J=2.5, 9.6, 17.8 Hz, 1H), 2.52 ('dt', J=3.0, 7.4 Hz, 2H), 2.58-2.67 (m, 1H), 2.60 (dd, J=9.3, 13.5 Hz, 1H), 2.86 (dd, J=2.6, 13.5 Hz, 1H), 4.21-4.27 (m, 1H); $^{13}$C NMR δ 14.0, 21.9, 22.6, 28.0, 28.7, 29.1, 29.2, 29.4, 29.8, 31.2, 31.8, 32.9, 35.5, 57.5, 83.0, 149.8, 174.0; MS (ESI) m/z 358 (10, MH$^+$), 299 (100, [MH−59]$^+$).

N-tert-Butoxycarbonyl-5-(dodecylthiomethyl)pyrrolidin-2-one [8d(5S)]. Treatment of 7d (234 mg, 0.78 mmol) in CH$_2$Cl$_2$ (5 mL) with DMAP (100 mg, 0.82 mmol), and (Boc)$_2$O (600 mg, 2.75 mmol) by procedure B [column chromatography (15→20% EtOAc/hexane)] gave 8d(5S) (302 mg, 97%) as a solidifying oil: $^1$H NMR δ 0.87 (t, J=7.0 Hz, 3H), 1.21-1.31 (m, 16H), 1.31-1.40 (m, 2H), 1.53 (s, 9H), 1.58 ('quint', J=7.5 Hz, 2H), 1.99-2.06 (m, 1H), 2.08-2.20 (m, 1H), 2.43 (ddd, J=2.5, 9.6, 17.9 Hz, 1H), 2.54 ('dt', J=2.9, 7.4 Hz, 2H), 2.60-2.70 (m, 2H), 2.62 (dd, J=9.2, 13.5 Hz, 1H), 2.89 (dd, J=2.6, 13.5 Hz, 1H), 4.23-4.29 (m, 1H); $^{13}$C NMR δ 14.1, 22.0, 22.7, 28.1, 28.8, 29.2, 29.3, 29.5, 29.6, 29.6, 29.6, 29.8, 31.2, 31.9, 32.9, 35.5, 57.5, 83.0, 149.8, 174.0; MS (ESI) m/z 400 (10, MH$^+$), 341 (100, [MH−59]$^+$).

5-(Hexylthiomethyl)pyrrolidin-2-ol[10b(5S)]. Treatment of 8b (178 mg, 0.56 mmol) in CH$_2$Cl$_2$ (3 mL) with LiEt$_3$BH (1M soln in THF, 1.41 mL, 1.41 mmol), by procedure C [quenched with MeOH (4 mL) at low temp., column chromatography (30→40% EtOAc/hexane)] gave N-tert-butoxycarbonyl-5-(hexylthiomethyl)pyrrolidin-2-ol[9b(5S); 170 mg, 95%)] as a colorless oil of a mixture of isomers: MS (ESI) m/z 316 (100, [M−1]$^+$), 300 (20, [M−17]$^+$). Treatment of 9b with an excess of TFA by Procedure D (step a, 2 h at rt) gave 10b as a light yellow oil as a mixture of isomers accompanied by ~22% of the open aldehyde form [$^1$H NMR δ 8.91 (s, ~0.22H)]: MS (ESI) m/z 200 (100, [M−17]$^+$). Crude product 10b was column chromatographed (60→70% EtOAc/hexane) and rechromatographed (0→0.25% MeOH/CHCl$_3$) to give pure azahemiacetal 10b (α/β, 0.45:1.0; 9.6 mg, 13%) as a colorless oil: δ $^1$H NMR δ 0.89 (t, J=7.0 Hz, 4.35H), 1.26-1.45 (m, 8.7H), 1.47-1.72 (m, 3.9H), 1.75-1.85 (m, 0.45H), 1.92-2.07 (m, 3.45H), 2.10-2.23 (m, 0.9H), 2.46 (dd, J=9.5, 13.0 Hz, 1H), 2.52-2.65 (m, 2.9H), 2.93-3.02 (m, 0.9H), 3.23 (dd, J=2.5, 13.0 Hz, 1H), 3.60-3.68 (m, 1H), 3.67-3.75 (m, 0.45H), 4.04-4.10 (m, 1H), 4.20-4.27 (m, 0.45H);

5-(Nonanylthiomethyl)pyrrolidin-2-ol[10c(5S)]. Treatment of 8c (227 mg, 0.64 mmol) in $CH_2Cl_2$ (4 mL) with LiEt$_3$BH (1M soln in THF, 1.59 mL, 1.59 mmol), by procedure C [quenched with MeOH (5 mL) at low temp., column chromatography (20→30% EtOAc/hexane)] gave tert-Butoxycarbonyl-5-(nonanylthiomethyl)pyrrolidin-2-ol[9c(5S); 220 mg, 96%] as a colorless oil of a mixture of isomers: MS (ESI) m/z 358 (10, [M−1]$^+$), 342 (100, [M−17]$^+$). Treatment of 9c with an excess of TFA by Procedure D (step a, 2 h at rt) gave 10c as a light yellow oil of a mixture of isomers accompanied by ~15% of the open aldehyde form [$^1$H NMR δ 8.87 (s, ~0.15H)]: MS (ESI) m/z 258 (15, [M−1]$^+$), 242 (100, [M−17]$^+$).

5-(Dodecylthiomethyl)pyrrolidin-2-ol[10d(5S)]. Treatment of 8d (224 mg, 0.56 mmol) in $CH_2Cl_2$ (4 mL) with LiEt$_3$BH (1M soln in THF, 1.4 mL, 1.4 mmol), by procedure C [quenched with MeOH (5 mL) at low temp., column chromatography (20→30% EtOAc/hexane)] gave N-tert-butoxycarbonyl-5-(dodecylthiomethyl)pyrrolidin-2-ol[9d(5S); (219 mg, 97%)] as a solidifying oil of a mixture of isomers: MS (ESI) m/z 400 (5, [M−1]$^+$), 384 (100, [M−17]$^+$). Treatment of 9d with an excess of TFA by Procedure D (step a, 2 h at rt) gave 10d as light yellow oil as a mixture of isomers accompanied by 8% of the open aldehyde form [$^1$H NMR δ 8.89 (s, ~0.08H)]): MS (ESI) m/z 301 (5, M$^+$), 300 (20, [M−1]$^+$), 284 (100, [M−17]$^+$).

N-tert-Butoxycarbonyl-1,4-dideoxy-1,4-imino-2,3-O-isopropylidene-5-O-methanesulfonyl-D-ribitol [12(3R,4R,5R)]. $^1$H NMR δ 1.28 (s, 3, $CH_3$), 1.42 (s, 12H, t-Bu, $CH_3$), 2.96 (s, 1.2, Ms), 2.98 (s, 1.8, Ms), 3.39 (dd, J=12.5, 4.8 Hz, 0.4H), 3.46 (dd, J=12.5, 4.8 Hz, 0.6H), 3.69 (d, J=12.5 Hz, 0.6H), 3.82 (d, J=12.5 Hz, 0.4H), 4.10-4.14 (m, 0.4H), 4.22-4.30 (m, 1H), 4.22-4.29 (m, 1.4H), 4.45 (dd, J=10.1, 4.1 Hz, 0.6H), 4.65 ('d', J=5.9 Hz, 1H); 4.72 ('t', J=5.3 Hz, 1H); $^{13}$C NMR (major rotamer) δ 24.9, 26.9, 29.6, 37.1, 52.5, 62.4, 68.9, 79.2, 80.4, 81.7, 112.1, 154.2; $^{13}$C NMR (minor rotamer) δ 24.9, 26.9, 29.6, 37.5, 53.1, 62.6, 68.6, 78.5, 80.6, 82.5, 112.1, 153.6; MS (APCI) m/z 352 (10, MH$^+$), 252 (100, [MH$_2$−Boc]$^+$).

N-(tert-Butoxycarbonyl)-3,4-dihydroxy-3,4-O-isopropylidene-5-(nonylthiomethyl)pyrrolidin-2-one [15(3R,4R,5S)]. Treatment of 13 (60 mg, 0.16 mmol) in dry DMF (0.5 mL) with nonathiolate [generated from nonanethiol (62 μL, 0.33 mmol)/NaH (14 mg, 0.35 mmol, 60%/mineral oil) in dry DMF (0.5 mL)] by Procedure A (column chromatography 5%→10% MeOH/EtOAc) gave 15 (30 mg, 42%) as a colorless oil: 1H NMR δ 0.87 (t, J=7.0 Hz, 3H), 1.25-1.31 (m, 12H), 1.36 (s, 3H), 1.45 (s, 3H), 1.56-1.57 (m, 11H), 2.44-2.54 (m, 2H), 2.82 (dd, J=6.2, 14.4 Hz, 1H), 2.91 (dd, J=2.7, 14.4 Hz, 1H), 4.38 (dd, J=2.7, 6.2 Hz, 1H), 4.45 (d, J=5.5 Hz, 1H), 4.85 (d, J=5.5 Hz, 1H); $^{13}$C NMR δ 14.1, 22.6, 28.7, 29.2, 29.2, 29.4, 31.8, 29.7, 24.4, 25.5, 27.0, 28.0, 33.7, 33.9, 60.8, 76.1, 77.6, 83.9, 112.3, 149.8, 170.6; MS (APCI) m/z m/z 330 (100, [MH$_2$−Boc]$^+$).

3,4-Dihydroxy-5-(nonylthiomethyl)pyrrolidin-2-one [17 (3R,4R,5S)]. Treatment of 15 (20 mg, 0.04 mmol) with TFA/$H_2$O (1 mL, 9:1), as described for 16, gave 17 (10 mg, 85%) as a colorless oil. $^1$H NMR δ 0.88 (t, J=6.8 Hz, 3H), 1.20-1.38 (m, 12H), 1.52-1.59 (m, 2H), 2.49-2.54 (m, 3H), 2.70 (dd, J=5.4, 13.5 Hz, 1H), 3.71 ('t', J=5.6 Hz, 1H), 4.25 (d, J=4.9 Hz, 1H), 4.49 (d, J=4.6 Hz, 1H), 7.15 (s, 1H); $^{13}$C NMR δ 14.1, 22.7, 28.8, 29.2, 29.3, 29.7, 31.9, 29.5, 27.0, 32.6, 35.0, 60.7, 69.7, 72.5, 176.2; MS (APCI) m/z 290 (100, [MH]$^+$).

3,4-Dihydroxy-5-(nonylthiomethyl)pyrrolidin-2-ol[21 (3R,4R,5S)]. Treatment of 15 (40 mg, 0.09 mmol) in THF (1 mL) with LiEt$_3$BH (1M/THF, 0.22 mL, 0.22 mmol), by procedure C [column chromatography (10→20% EtOAc/hexane)] gave N-(tert-butoxycarbonyl)-3,4-dihydroxy-3,4-O-isopropylidene-5-nonylthiomethyl-pyrrolidine-2-ol [19(3R, 4R,5S)]; 30 mg, 75%)] as a colorless oil as a mixture of isomers: MS (APCI) m/z 414 (100, [M−17]$^+$), 314 (95, [MH−Boc−17]$^+$). Deprotection of 19 (28 mg, 0.06 mmol) with an excess of TFA/$H_2$O (0.9:0.1 mL) by Procedure D gave a light yellow oil that was column chromatographed (5→10% MeOH/EtOAc) to give 21 (18 mg, 96%) as a light yellow oil. 1H NMR showed a complex mixture of isomers: MS (APCI) m/z 292 (100, MH$^+$), 274 (60, [M−17]$^+$).

Biological Assays:

Anti-Quorum Sensing Assay (β-Galactosidase Assay). An overnight (O/N) culture of *Escherichia coli* DH5α harboring the plasmids pSC11, which contains a $P_{lasI}$-lacZ translational fusion (24), and pJN105L, which contains a $P_{BAD}$-lasR expression plasmid (25) grown in LB media (10 g tryptone, 5 g yeast extract, 5 g sodium chloride per liter) supplemented with ampillicin (100 μg/ml) and gentamycin (15 μg/ml), was diluted to an OD$_{600}$ of 0.150. At this time, arabinose (0.2% w/v), N-3-(oxododecanoyl)homoserine lactone (3-oxo-C$_{12}$-AHL; 2 μM), and either the compound under analysis or solvent (DMSO), was added to the culture (1.5 mL). A negative control containing only solvent and arabinose (0.2% w/v) was also assayed. The cultures were incubated with shaking for three hours at 37° C.

The conditions for the rhl biomonitor *Escherichia coli* DH5α harboring pECP61.5 plasmid, which contains $P_{tac}$-rhlR and $P_{rhlA}$-lacZ (4), were essentially same except that the LB medium was only supplemented with ampillicin (100 μg/ml), the O/N culture was diluted to an OD$_{600}$ of 0.150, induced with 1 mM IPTG, 2 μM C$_4$—HSL and the compounds or the controls added when the OD$_{600}$ reached 1.0. After incubation at 37° C. for 4 hours with shaking, β-galactosidase activity was assayed as described previously (28). Miller units were calculated as described (29). Assays were repeated at least twice. For each biological replicate, experimental triplicates were performed and the average percent activity calculated by dividing the average Miller units from the samples containing compound or extract by the average Miller units from the sample containing solvent and multiplying by 100. Significance of inhibition was determined using a paired two-tailed Student t-test.

Luminescence Assay: *Vibrio harveyi* was grown in AB medium. A 2.5 mL aliquot of overnight culture of *V. harveyi* was added to 2.5 μL and 10 μL of each compound as well as the solvent. The compound was dissolved in water or DMSO to serve as a control. Growth and luminescence were measured simultaneously in a modified Spec20 for three hours. Growth was measured as OD$_{600}$ and luminescence was recorded in light units (1 LU=6.51×10$^8$ quanta/sec/mL).

Strains: *E. coli* DH5α harboring a $P_{BAD}$-lasR expression plasmid and a $P_{lasI}$-lacZ translational fusion plasmid was used as a biomonitor for the *P. aeruginosa* Las QS system, and *e. coli* XL-1Blue harboring a plasmid containing rhlA::lacZ translational fusion and $P_{tac}$-rhlR was used as a biomonitor for the *P. aeruginosa* Rhl QS system. *V. harveyi* strain B392 (MAV) was used.

Example 2

Substituted Lactam and Cyclic Azahemiacetals Modulate *Pseudomonas Aeruginosa* Quorum Sensing In this work, a set of optically pure γ-lactams and their reduced cyclic azahemiacetal analogues were synthesized, bearing the additional alkylthiomethyl substituent, and evaluated their effect on *P. aeruginosa* AHL-dependent las and rhl QS pathways. The concentration of these ligands and the simple structural modification such as the length of the alkylthio substituent has notable effect on activity. The γ-lactam derivatives with nonanylthio or dodecylthio chains acted as inhibitors of las signaling with moderate potency. The cyclic azahemiacetal with shorter propylthio or hexylthio substituent was found to strongly inhibit both las and rhl signaling at higher concentrations while the propylthio analogue strongly stimulated the las QS system at lower concentrations (50 μg/mL).

Design and Synthesis. The (S)-5-(bromomethyl)pyrrolidin-2-one (6), a key substrate for the synthesis of γ-lactam analogue 7 was conveniently prepared from L-pyroglutamic acid (17). Displacement of bromide in 6 with sodium propanethiolate produced 5(S)-(propylthiomethyl)pyrrolidin-2-one (7a, 96%; Scheme 1). Since it was previously demonstrated that the length of the side chain is crucial for determining the agonistic and antagonistic activity (18), lactams containing C6, C9 and C12 alkylthio chain lengths (7b-d) were also analogously prepared. A set of the cyclic azahemiacetals (N,O-acetals or hemiaminals) 10 with a hydroxyl group instead of a carbonyl oxygen at C2 was synthesized as well. Thus, although, attempted reduction of lactams (7) with LiBEt₃H was unsuccessful, reduction of the N-Boc protected lactams 8a-d proceeded smoothly to afford azahemiacetals 9a-d. Subsequent deprotection with trifluoroacetic acid afforded 5(S)-(alkylthiomethyl)pyrrolidin-2-ol 10a-d as a mixture of isomers.

Scheme 1.

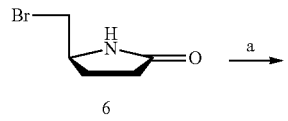

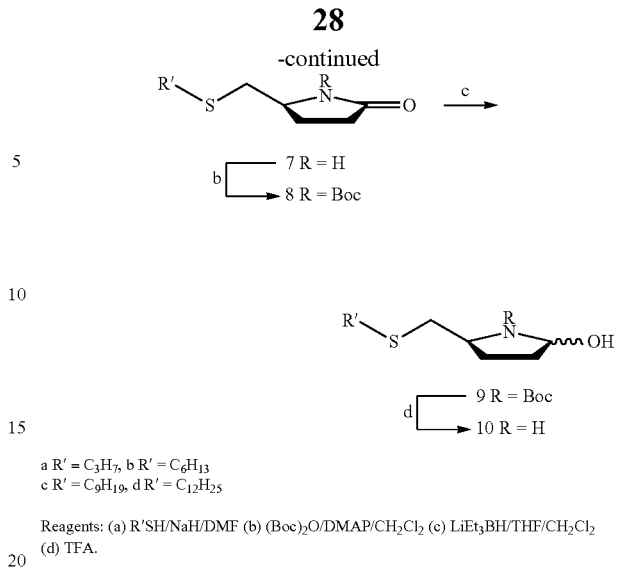

a R' = C₃H₇, b R' = C₆H₁₃
c R' = C₉H₁₉, d R' = C₁₂H₂₅

Reagents: (a) R'SH/NaH/DMF (b) (Boc)₂O/DMAP/CH₂Cl₂ (c) LiEt₃BH/THF/CH₂Cl₂ (d) TFA.

To increase the polarity/solubility of the lactam and azahemiacetal analogues in the testing media, aza analogues with hydroxyl groups at C3 and C4 were also prepared. The N-Boc protected 1,4-dideoxy-1,4-imino-D-ribitol (11) (19-21), conveniently prepared from D-gulonic-g-lactone, served as a suitable starting material for the synthesis of dihydroxy γ-lactams 14 and 15. Thus, mesylation of ribitol 11 followed by the selective oxidation (22) of the resulting 12 afforded 13. Displacement of the mesylate 13 with sodium hexane- and nonanethiolate produced 5-alkylthiomethyl lactams 14 and 15 in high yields which were deprotected with TFA to give (5S)-(hexyl- or nonanylthiomethyl)-3,4-dihydroxypyrrolidin-2-ones 16 and 17 (Scheme 2). Reduction of 5-alkylthiomethyl lactams 14 and 15 with LiBEt3H afforded cyclic azahemiacetals 18 and 19. Subsequent deprotection with TFA provided (5S)-(alkylthiomethyl)-3,4-dihydroxypyrrolidin-2-ols 20 and 21 as a complex mixture of azahemiacetals existing in equilibrium with dehydrated form (imine) as well as with open aldehyde and dimeric forms, as reported for such class of 4-azaribofuranoses (23). These azahemiacetals can be considered as aza analogues of S-ribosyl-L-homocysteine (SRH) in which (a) ribose oxygen is replaced by nitrogen atom and (b) the homocysteine moiety is substituted with n-alkylthiols with different length of carbon chain.

Scheme 2.

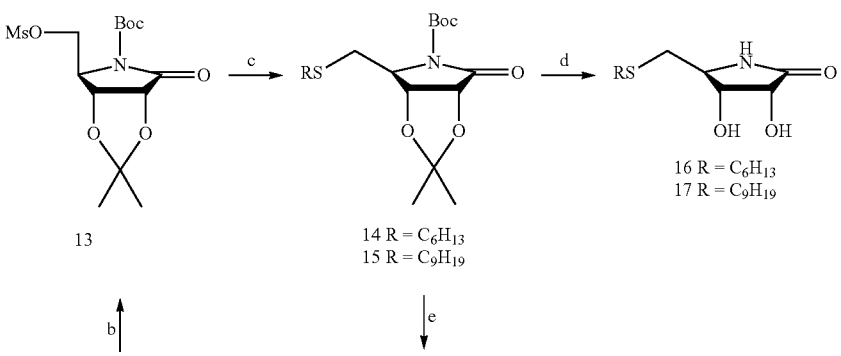

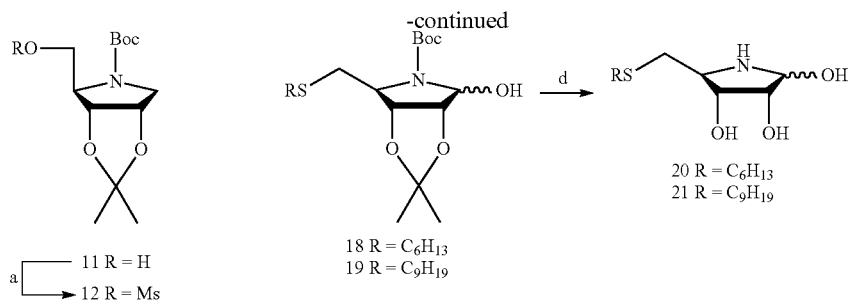

Reagents: (a) MsCl/NEt₃/CH₂Cl₂/rt (b) NaIO₄/hydrated RuO₂/EtOAc/H₂O/rt. (C) RSH/NaH/DMF. (d) TFA/H₂O.(e) LiEt₃BH/THF/CH₂Cl₂

Figure 2:
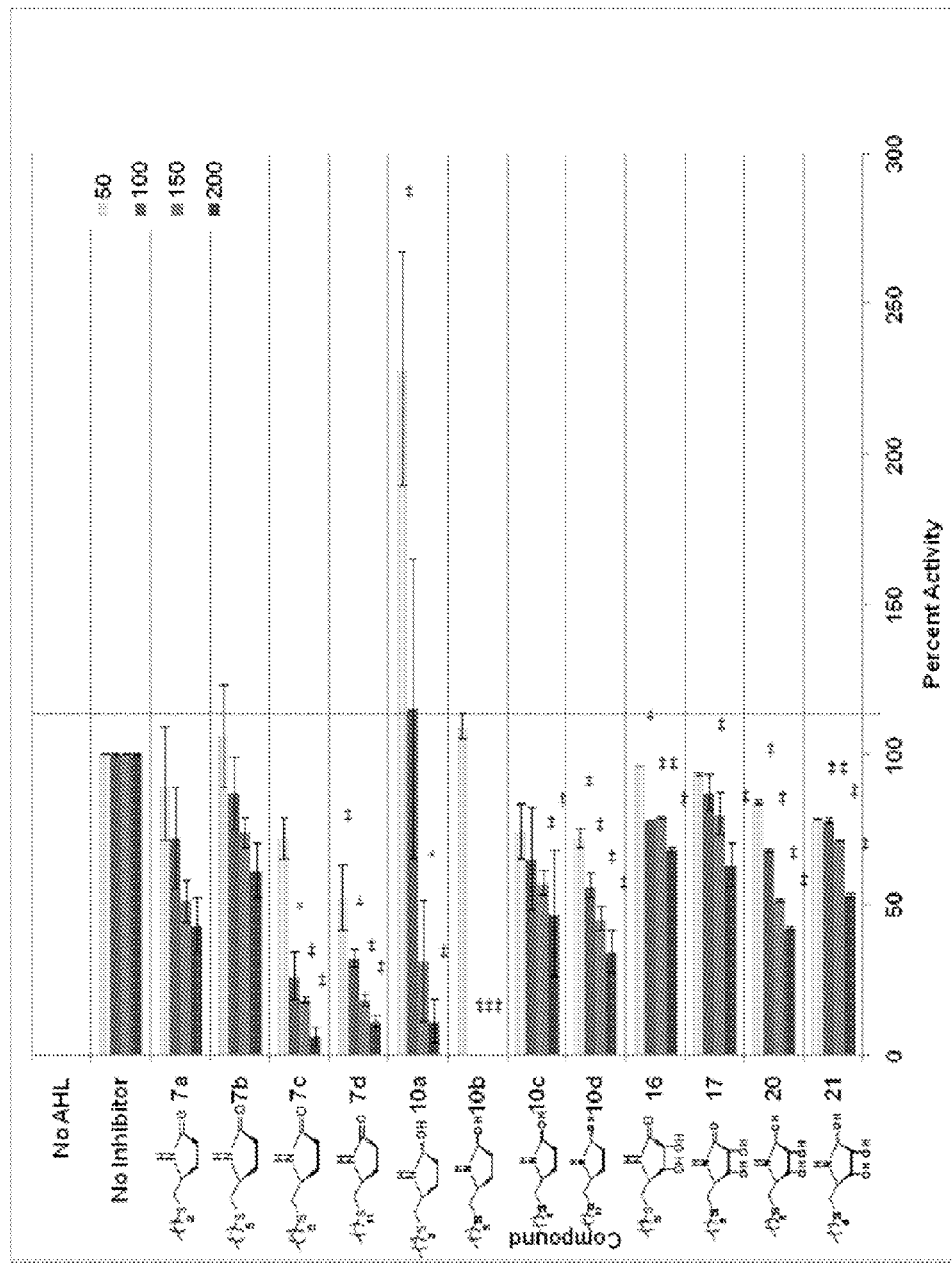
FIG. 2 shows the effect of lactam and cyclic azahemiacetal derivatives on $P_{lasI}$-lacZ expression in E. coli tested at 50-200 µg/mL concentrations against 2 µM of 3-oxo-$C_{12}$-AHL. $P_{lasI}$-lacZ activity is depicted as percent activity relative to the DMSO treated control. Significance was determined by a paired two-tailed Student t-test and is denoted as follows: *p-value<0.05, †p-value<0.02, ‡p-value<0.01.

Screening against las signaling. To determine the effect of the lactams (7, 16, and 17) and the cyclic azahemiacetal derivatives (10, 20 and 21) on the *P. aeruginosa* las AHL-mediated pathway, a las-dependent β-galactosidase reporter ($P_{las}$I-lacZ) was expressed with lasR in *E. coli* (24-25). As expected, and in agreement with published data (24-25), exogenous 3-oxo-$C_{12}$-AHL activated the $P_{lasI}$-lacZ (FIG. 2). Also, no activity was observed in absence of exogenous AHL. The effect of synthetic compounds on the las activity was also compared with the addition of DMSO as a solvent. The propylthio lactam 7a and its azahemiacetal counterpart 10a were initially screened at a concentration of 100 μg/mL for their activity against the las system. The lactam 7a inhibited las activity approximately by 28%, while the azahemiacetal 10a was found to enhance las reporter activity by 15%. This was dependent upon the addition of 2 μM of 3-oxo-$C_{12}$-AHL. However, azahemiacetal 10a significantly stimulated (approximately by 2.3-fold) las reporter activity at the concentration of 50 μg/mL, while inhibiting las reporter activity by 69% and 89% at 150 and 200 μg/mL, respectively. In contrast, the lactam analogue 7a inhibited las activity at all concentrations tested. Cell growth was not inhibited by the addition of lactam and azahemiacetal compounds at the tested concentrations (data not shown).

Among other lactam analogues tested, the percent inhibition increased in a concentration dependent manner. Inhibition potency also increased as the alkylthio chain length increased. Specifically, nonylthio lactam 7c and dodecylthio lactam 7d were found to possess greatest inhibition at all concentrations tested. At the lowest concentration tested (50 μg/mL), nonylthio lactam 7c inhibited 28% while dodecylthio lactam 7d inhibited 48%. On the contrary, among the cyclic azahemiacetals analogues, no general trend was observed between chain length and percent inhibition. As with the propylthio azahemiacetal 10a, hexylthio azahemiacetal 10b also stimulated QS at 50 μg/mL but with much lesser potency and inhibited 100% at all higher concentrations tested. Azahemiacetals containing nonyl side chain 10c and dodecyl chain 10d showed moderate activity. The ribolactam analogues 16 and 17 and their cyclic azahemiacetal counterparts 20 and 21 were found to inhibit las activity at all concentrations tested but only with moderate potency with azahemiacetals being slightly more active.

TABLE 1

Effect of lactam and cyclic azahemiacetal analogues on rhl signaling

| | Concentration (μg/mL) | | | |
|---|---|---|---|---|
| | 50 | 100 | 150 | 200 |
| Compound | Percent Activity[a,b] ± Standard Deviation | | | |
| 7a | 104 ± 24 | 118 ± 0.8 | 104 ± 13 | 108 ± 17 |
| 7b | 126 ± 8 | 126 ± 29 | 130 ± 31 | 145[‡] ± 19 |

TABLE 1-continued

Effect of lactam and cyclic azahemiacetal analogues on rhl signaling

| | Concentration (μg/mL) | | | |
|---|---|---|---|---|
| | 50 | 100 | 150 | 200 |
| Compound | Percent Activity[a,b] ± Standard Deviation | | | |
| 7c | 95 ± 3 | 115 ± 30 | 108 ± 12 | 137 ± 46 |
| 7d | 103 ± 7 | 106 ± 6 | 109 ± 8 | 106 ± 5 |
| 10a | 121 ± 6 | 138 ± 3 | 41[†] ± 1 | 9 ± 1[‡] |
| 10b | 26 ± 0.2 | 0.2[†] ± 0.3 | 0[‡] ± 0 | 0* ± 0 |
| 10c | 93 ± 12 | 80 ± 13 | 100 ± 11 | 99 ± 3 |
| 10d | 98 ± 13 | 93 ± 27 | 91 ± 8 | 96 ± 5 |
| 16 | 132 ± 36 | 129 ± 10 | 148 ± 9 | 161 ± 7[‡] |
| 17 | 106 ± 3 | 117[‡] ± 8 | 115 ± 11 | 135 ± 5[‡] |
| 20 | 94 ± 8 | 105 ± 3 | 109 ± 12 | 116 ± 18 |
| 21 | 98 ± 5 | 127* ± 14 | 116 ± 9 | 121 ± 14 |

[a]Effect of lactam and cyclic azahemiacetal derivatives on $P_{rhlA}$-lacZ expression in *E. coli* tested at 50-200 μg/mL concentrations against 2 μM of $C_4$-AHL as percent of activity relative to the DMSO treated control.
[b]*p-value < 0.05,
[†]p-value < 0.02,
[‡]p-value < 0.01 according to a paired, two-tailed Student t-test.

Screening Against the rhl Pathway. To determine the effect of the lactams (7, 16, and 17) and the cyclic azahemiacetal derivatives (10, 20 and 21) on the *P. aeruginosa* rhl AHL-mediated pathways, a rhl-dependent β-galactosidase reporter ($P_{rhlA}$-lacZ) was expressed with rhlR in *E. coli* (24-25). As expected, and in agreement with published data (24-25), exogenous $C_4$-AHL activated the rhl β-galactosidase reporter (data not shown). The lactam analogues 7a-d stimulated rhl QS activities at higher concentrations with moderate potency. Of these, hexylthio lactam 7b was most active (Table 2). In contrast, cyclic azahemiacetals with shorter alkylthio chain 10a and 10b inhibited rhl activity, while analogues with longer alkyl chain 10c and 10d were inactive. The hexylthio azahemiacetal 10b completely inhibited rhl signaling at concentrations of 100 μg/mL and higher. The strong inhibition observed with propylthio 10a and hexylthio 10b azahemiacetal analogues having side chain lengths similar to $C_4$-AHL is in agreement with the structure activity relationship reported for various synthetic AHL mimetics targeting RhlR (26). The ribolactam analogues 16 and 17 and their cyclic azahemiacetal counterparts 20 and 21 stimulated rhl activities with moderate potency with lactams being more effective (e.g., 16 vs. 20).

REFERENCES

1. Ng, W. L., and Bassler, B. L. (2009) Bacterial quorum-sensing network architectures, Annu. Rev. Genet. 43, 197-222.
2. Raffa, R. B., Iannuzzo, J. R., Levine, D. R., Saeid, K. K., Schwartz, R. C., Sucic, N. T., Terleckyj, O. D., and Young, J. M. (2005) Bacterial Communication ("Quorum Sensing") via Ligands and Receptors: A Novel Pharmacologic Target for the Design of Antibiotic Drugs, J. Pharmacol. Exp. Ther. 312, 417-423.
3. Williams, P., and Camara, M. (2009) Quorum sensing and environmental adaptation in *Pseudomonas aeruginosa*: a tale of regulatory networks and multifunctional signal molecules, Curr. Opin. Microbiol. 12, 182-191.
4. Pearson, J. P., Pesci, E. C., and Iglewski, B. H. (1997) Roles of *Pseudomonas aeruginosa* las and rhl quorum-sensing systems in control of elastase and rhamnolipid biosynthesis genes, J. Bacteriol. 179, 5756-5767.
5. Dekimpe, V., and Deziel, E. (2009) Revisiting the quorum-sensing hierarchy in *Pseudomonas aeruginosa*: the transcriptional regulator RhlR regulates LasR-specific factors, Microbiology 155, 712-723.
6. Bjarnsholt, T., Tolker-Nielsen, T., Hoiby, N., and Givskov, M. (2010) Interference of *Pseudomonas aeruginosa* signalling and biofilm formation for infection control, Expert. Rev. Mol. Med. 12, e11.
7. Geske, G. D., O'Neill, J. C., Miller, D. M., Mattmann, M. E., and Blackwell, H. E. (2007) Modulation of Bacterial Quorum Sensing with Synthetic Ligands: Systematic Evaluation of N-Acylated Homoserine Lactones in Multiple Species and New Insights into Their Mechanisms of Action, J. Am. Chem. Soc. 129, 13613-13625.
8. Amara, N., Mashiach, R., Amar, D., Krief, P., Spieser, S. p. A. H., Bottomley, M. J., Aharoni, A., and Meijler, M. M. (2009) Covalent Inhibition of Bacterial Quorum Sensing, J. Am. Chem. Soc. 131, 10610-10619.
9. Smith, K. M., Bu, Y., and Suga, H. (2003) Induction and Inhibition of *Pseudomonas aeruginosa* Quorum Sensing by Synthetic Autoinducer Analogs, Chem. Biol. 10, 81-89.
10. Muh, U., Schuster, M., Heim, R., Singh, A., Olson, E. R., and Greenberg, E. P. (2006) Novel *Pseudomonas aeruginosa* Quorum-Sensing Inhibitors Identified in an Ultra-High-Throughput Screen, Antimicrob. Agents Chemother. 50, 3674-3679.
11. Morohoshi, T., Shiono, T., Takidouchi, K., Kato, M., Kato, N., Kato, J., and Ikeda, T. (2007) Inhibition of Quorum Sensing in *Serratia marcescens* AS-1 by Synthetic Analogs of N-Acylhomoserine Lactone, Appl. Environ. Microbiol. 73, 6339-6344.
12. Ishida, T., Ikeda, T., Takiguchi, N., Kuroda, A., Ohtake, H., and Kato, J. (2007) Inhibition of Quorum Sensing in *Pseudomonas aeruginosa* by N-Acyl Cyclopentylamides, Appl. Environ. Microbiol. 73, 3183-3188.
13. Schaefer, A., Hanzelka, B., Eberhard, A., and Greenberg, E. (1996) Quorum sensing in *Vibrio fischeri*: probing autoinducer-LuxR interactions with autoinducer analogs, J. Bacteriol. 178, 2897-2901.
14. Chen, X., Schauder, S., Potier, N., Van Dorsselaer, A., Pelczer, I., Bassler, B. L., and Hughson, F. M. (2002) Structural identification of a bacterial quorum-sensing signal containing boron, Nature 415, 545-549.
15. Gopishetty, B., Zhu, J., Rajan, R., Sobczak, A. J., Wnuk, S. F., Bell, C. E., and Pei, D. (2009) Probing the Catalytic Mechanism of S-Ribosylhomocysteinase (LuxS) with Catalytic Intermediates and Substrate Analogues, J. Am. Chem. Soc. 131, 1243-1250.
16. Wnuk, S. F., Robert, J., Sobczak, A. J., Meyers, B. P., Malladi, V. L. A., Zhu, J., Gopishetty, B., and Pei, D. (2009) Inhibition of S-ribosylhomocysteinase (LuxS) by substrate analogues modified at the ribosyl C-3 position, Bioorg. Med. Chem. 17, 6699-6706.
17. Otsuka, M., Masuda, T., Haupt, A., Ohno, M., Shiraki, T., Sugiura, Y., and Maeda, K. (1990) Synthetic studies on antitumor antibiotic, bleomycin. 27. Man-designed bleomycin with altered sequence specificity in DNA cleavage, J. Am. Chem. Soc. 112, 838-845.
18. Passador, L., Tucker, K. D., Guertin, K. R., Journet, M. P., Kende, A. S., and Iglewski, B. H. (1996) Functional analysis of the *Pseudomonas aeruginosa* autoinducer PAI, J. Bacteriol. 178, 5995-6000.
19. Fleet, G. W. J., and Son, J. C. (1988) Polyhydroxylated pyrrolidines from sugar lactones: Synthesis of 1,4-dideoxy-1,4-imino-D-glucitol from D-galactonolactone and syntheses of 1,4-dideoxy-1,4-imino-D-allitol, 1,4-dideoxy-1,4-imino-D-ribitol, and (2S,3R,4S)-3,4-dihydroxyproline from D-gulonolactone, Tetrahedron 44, 2637-2647.
20. Murruzzu, C., and Riera, A. (2007) Enantioselective synthesis of hydroxylated pyrrolidines via Sharpless epoxidation and olefin metathesis, Tetrahedron: Asymmetry 18, 149-154.
21. Haidle, A. M., and Myers, A. G. (2004) An enantioselective, modular, and general route to the cytochalasins: Synthesis of L-696,474 and cytochalasin B, Proc. Natl. Acad. Sci. USA. 101, 12048-12053.
22. Qiu, X. L., and Qing, F. L. (2005) Synthesis of 3'-Deoxy-3'-difluoromethyl Azanucleosides from trans-4-Hydroxy-L-proline, J. Org. Chem. 70, 3826-3837.
23. Witte, J. F., and McClard, R. W. (1991) Synthesis of a potent [alpha]-glucosidase inhibitor epimeric to FR 900483, Tetrahedron Lett. 32, 3927-3930.
24. Chugani, S. A., Whiteley, M., Lee, K. M., D'Argenio, D., Manoil, C., and Greenberg, E. P. (2001) QscR, a modulator of quorum-sensing signal synthesis and virulence in *Pseudomonas aeruginosa*, Proc. Natl. Acad. Sci. USA. 98, 2752-2757.
25. Lee, J. H., Lequette, Y., and Greenberg, E. P. (2006) Activity of purified QscR, a *Pseudomonas aeruginosa* orphan quorum-sensing transcription factor, Mol. Microbiol. 59, 602-609.
26. Geske, G. D., O'Neill, J. C., and Blackwell, H. E. (2008) Expanding dialogues: from natural autoinducers to non-natural analogues that modulate quorum sensing in Gram-negative bacteria, Chem. Soc. Rev. 37, 1432-1447.
27. Pearson, J. P., Van Delden, C., and Iglewski, B. H. (1999) Active efflux and diffusion are involved in transport of *Pseudomonas aeruginosa* cell-to-cell signals, J. Bacteriol. 181, 1203-1210.
28. Mathee, K., and Howe, M. M. (1990) Identification of a positive regulator of the Mu middle operon, J. Bacteriol. 172, 6641-6650.
29. Miller, J. H. (1972) Experiments in molecular genetics, Cold Spring Harbor Laboratory, Cold Spring Harbor.

What is claimed:
1. A compound having a structure selected from

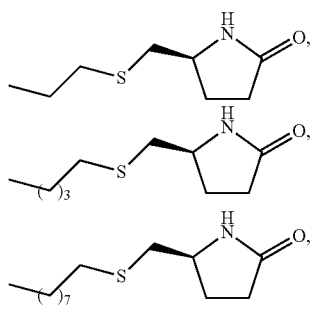

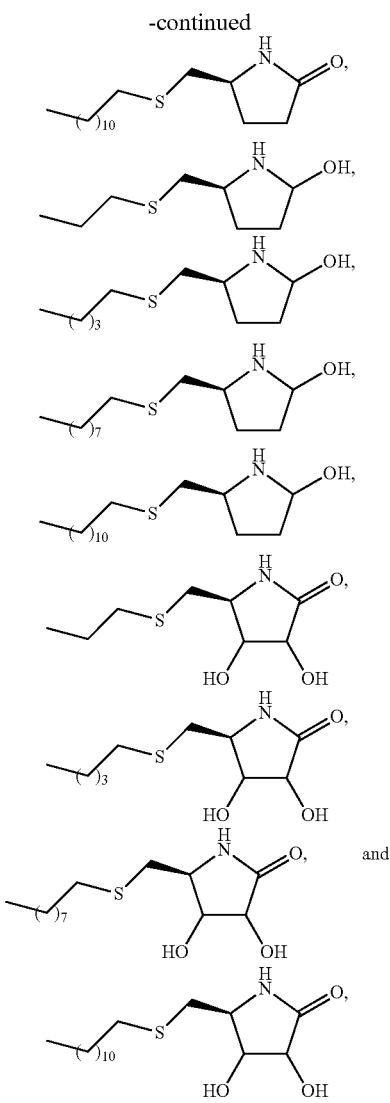

or a pharmaceutically acceptable salt thereof.

2. A pharmaceutical composition comprising the compound of claim 1 and a pharmaceutically acceptable excipient.

3. A method of inhibiting bacterial quorum sensing comprising contacting bacteria with the compound of claim 1.

4. The method of claim 3, wherein the bacteria is selected from the group consisting of : *Acinetobacter baumannii, Aeromonas hydrophila, Aeromonas salmonicida, Agrobacterium tumefaciens, Brucella melitensis, Burkholderia cenocepacia, Burkholderia mallei, Burkholderia pseudomallei, Burkholderia vietnamiensis, Chromobacterium violaceum, Enterobacter agglomeran, Erwinia carotovora, Erwinia chrysanthemi, Escherichia coli, Nitrosomas europaea, Obesumbacterium proteus, Pantoea agglomerans, Pantoea stewartii, Pseudomonas aureofaciens, Pseudomonas aeruginosa, Pseudomonas fluorescens, Pseudomonas fuscovaginae, Pseudomonas syringae, Ralstonia solanacearum, Rhizobium etli, Rhizobium leguminosarum, Rhodobacter sphaeroides, Serratia liquefaciens, Serratia marcescens, Vibrio anguillarum, Vibrio fischeri, Vibrio parahaemolyticus, Vibrio salmonicida, Xanthomonas campestris, Xenorhabdus nematophilus, Yersinia enterocolitica, Yersinia pestis, Yersinia pseudotuberculosis, Yersinia medievalis, Yersinia ruckeri*, and combinations thereof.

5. The method of claim 3, wherein the contacting comprises administering the compound or the composition to a subject suffering from a bacterial infection.

6. The method of claim 5, further comprising administering a second agent to the subject.

7. The method of claim 6, wherein the second agent is an antibiotic.

8. The method of claim 7, wherein the antibiotic is selected from a penicillin, a selexcid, a cephalosporin, a tetracycline, a rifamycin, gentamycin, clindamycin, a fluoroquinolone, a monobactamer, a carbapeneme, a macrolide, a polymyxin, an aminoglycoside, tobramycin, a sulfonamide, a fusidine, a vancomycin, an oxazolidinone, a metronidazole, a corticosteroid, hydrocortisone, triamcinolone, betamethasone, and combinations thereof.

9. A method of treating a subject suffering from an infection comprising administering to the subject an effective amount of the compound of claim 1.

10. The method of claim 9, further comprising administering to the subject a second therapeutic.

11. The method of claim 10, wherein the second therapeutic is an antibiotic.

12. The method of claim 11, wherein the antibiotic is selected from a penicillin, a selexcid, a cephalosporin, a tetracycline, a rifamycin, gentamycin, clindamycin, a fluoroquinolone, a monobactamer, a carbapeneme, a macrolide, a polymyxin, an aminoglycoside, tobramycin, a sulfonamide, a fusidine, a vancomycin, an oxazolidinone, a metronidazole, a corticosteroid, hydrocortisone, triamcinolone, betamethasone, and combinations thereof.

13. The method of claim 9, wherein the infection is a *P. aeruginosa* infection.

14. A method of inhibiting formation of a biofilm comprising contacting bacteria the compound of claim 1.

15. The method of claim 14, wherein the contacting comprises administering the compound or the composition to a subject suffering from a bacterial infection.

* * * * *